(12) United States Patent
Burkholz et al.

(10) Patent No.: US 11,337,628 B2
(45) Date of Patent: May 24, 2022

(54) SYRINGE-BASED DELIVERY DEVICE FOR A VASCULAR ACCESS INSTRUMENT

(71) Applicant: Becton, Dickinson and Company, Franklin Lakes, NJ (US)

(72) Inventors: Jonathan Karl Burkholz, Salt Lake City, UT (US); Derek Jewell, Cottonwood Heights, UT (US); Joseph Spataro, Cottonwood Heights, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 371 days.

(21) Appl. No.: 16/691,217

(22) Filed: Nov. 21, 2019

(65) Prior Publication Data

US 2020/0170559 A1 Jun. 4, 2020

Related U.S. Application Data

(60) Provisional application No. 62/773,029, filed on Nov. 29, 2018.

(51) Int. Cl.
*A61B 5/15* (2006.01)
*A61M 5/31* (2006.01)
*A61M 25/06* (2006.01)

(52) U.S. Cl.
CPC ..... *A61B 5/150992* (2013.01); *A61M 5/3137* (2013.01); *A61M 5/3148* (2013.01); *A61M 25/0606* (2013.01); *A61M 2005/3132* (2013.01)

(58) Field of Classification Search
CPC ............ A61M 25/0113; A61M 5/3137; A61M 25/0606; A61M 5/3148; A61B 5/150992
See application file for complete search history.

(56) References Cited

U.S. PATENT DOCUMENTS

| | | | |
|---|---|---|---|
| 4,464,171 A | 8/1984 | Garwin | |
| 8,366,685 B2 | 2/2013 | Devgon | |
| 9,186,100 B2 | 11/2015 | Devgon | |
| 9,744,344 B1 | 8/2017 | Devgon et al. | |
| 2014/0188002 A1 | 7/2014 | Close et al. | |
| 2015/0224287 A1* | 8/2015 | Bian | A61M 25/065 604/218 |
| 2017/0216564 A1 | 8/2017 | Devgon et al. | |
| 2017/0360345 A1 | 12/2017 | Devgon | |
| 2018/0221578 A1* | 8/2018 | Hopkins | A61B 5/150992 |
| 2018/0272106 A1* | 9/2018 | Funk | A61M 25/0113 |

\* cited by examiner

*Primary Examiner* — Bhisma Mehta
*Assistant Examiner* — John J Crawford
(74) *Attorney, Agent, or Firm* — Kirton McConkie; Whitney Blair; Kevin Stinger

(57) ABSTRACT

A delivery device for delivering an instrument into a catheter assembly may include a syringe having a barrel and a plunger movable within the barrel. In response to depression of the plunger within the barrel, an instrument may be advanced distally. The instrument may include a catheter, a probe, a light tube for disinfection, or another suitable instrument. In response to depression of the plunger within the barrel, a distal end of the instrument may move through a catheter assembly coupled to the delivery device and into vasculature of a patient.

12 Claims, 17 Drawing Sheets

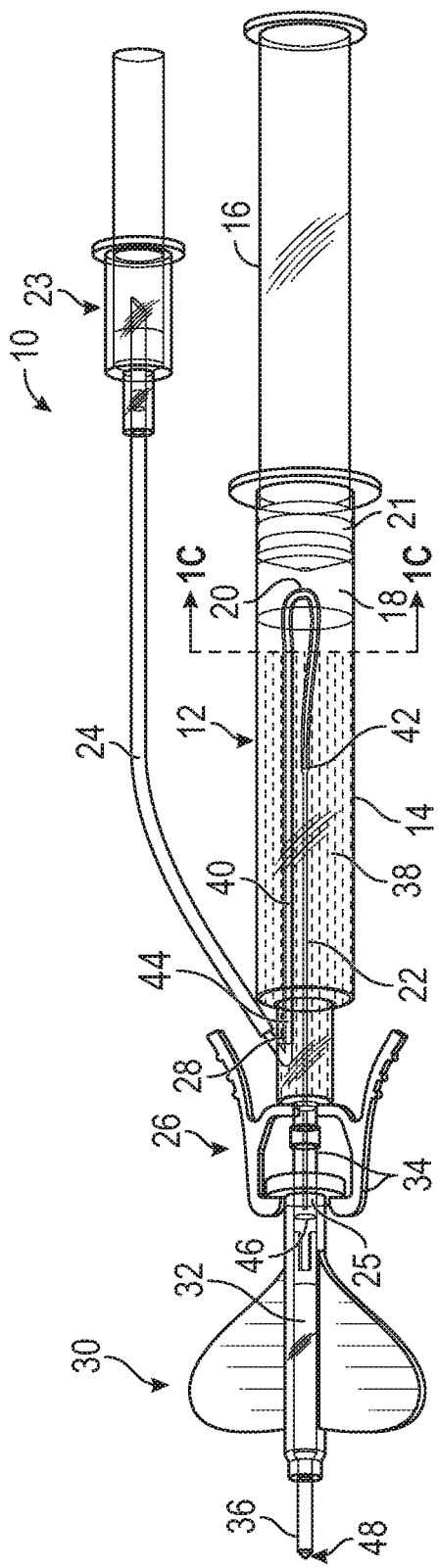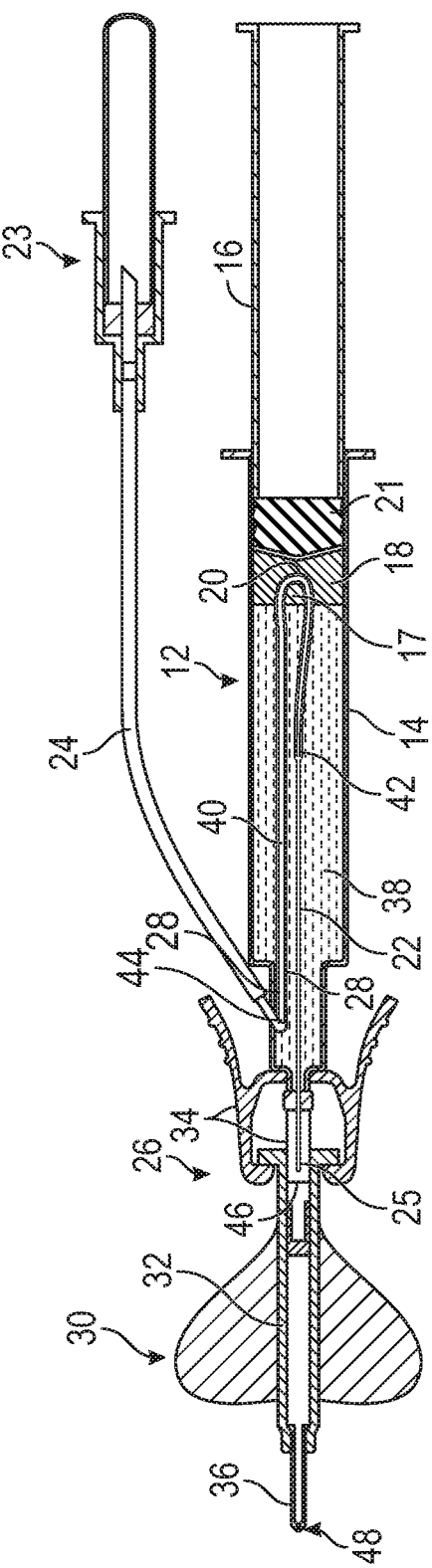
FIG. 1A
FIG. 1B

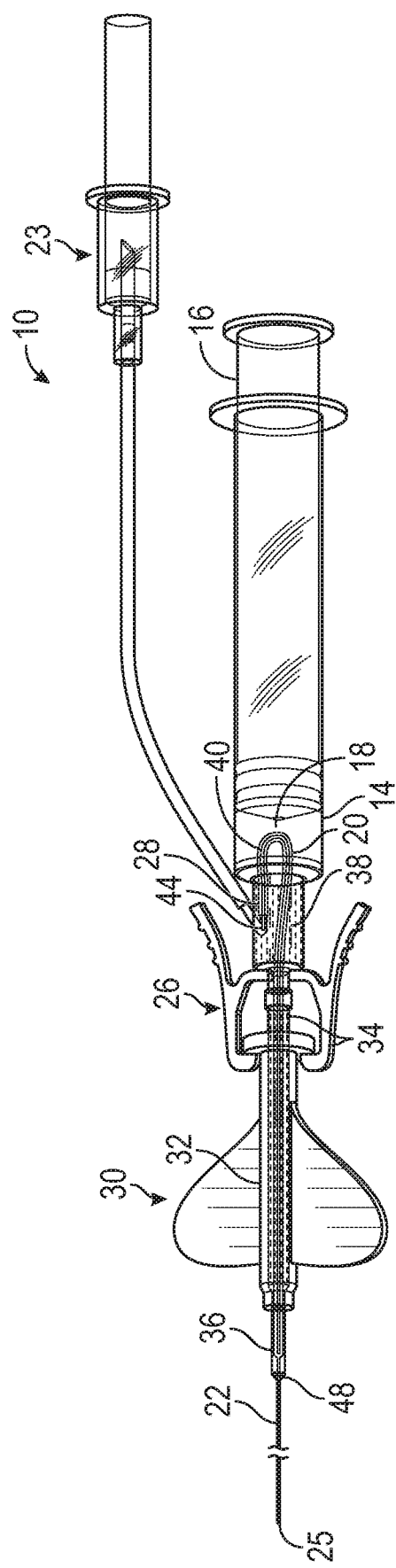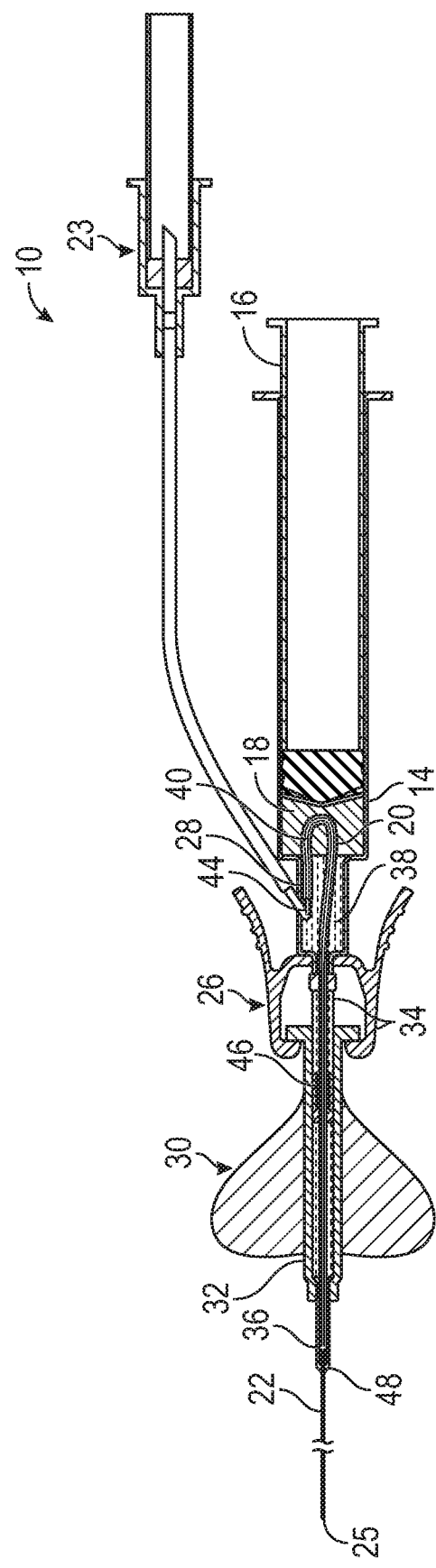

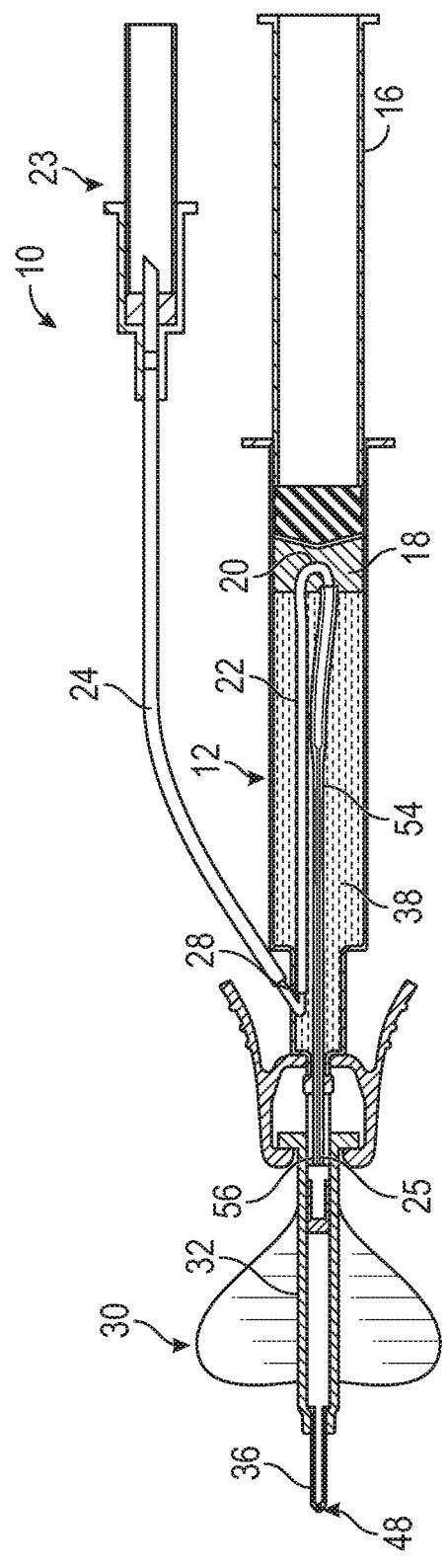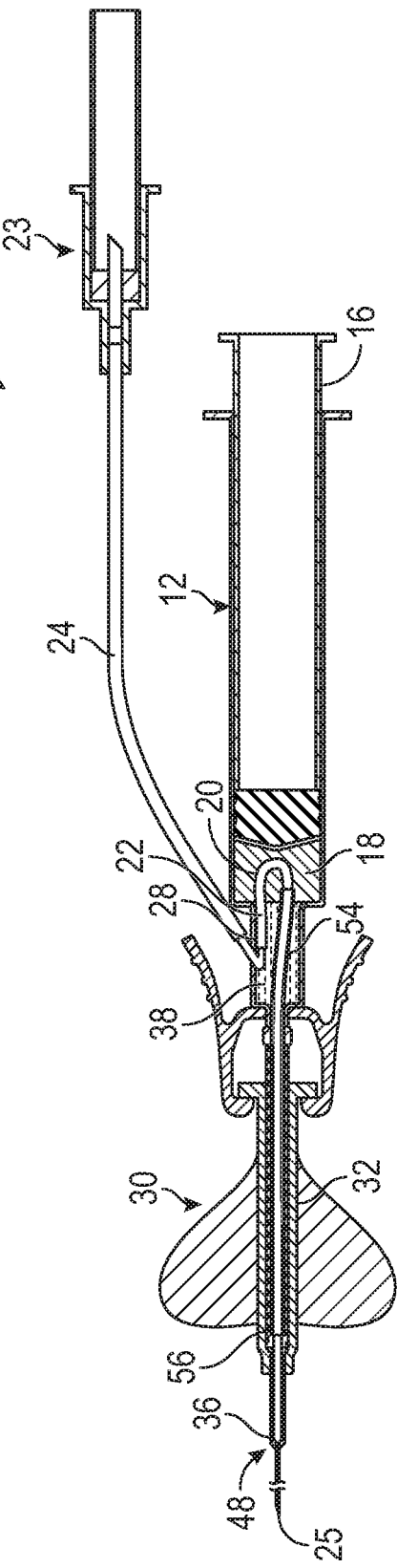
FIG. 3A
FIG. 3B

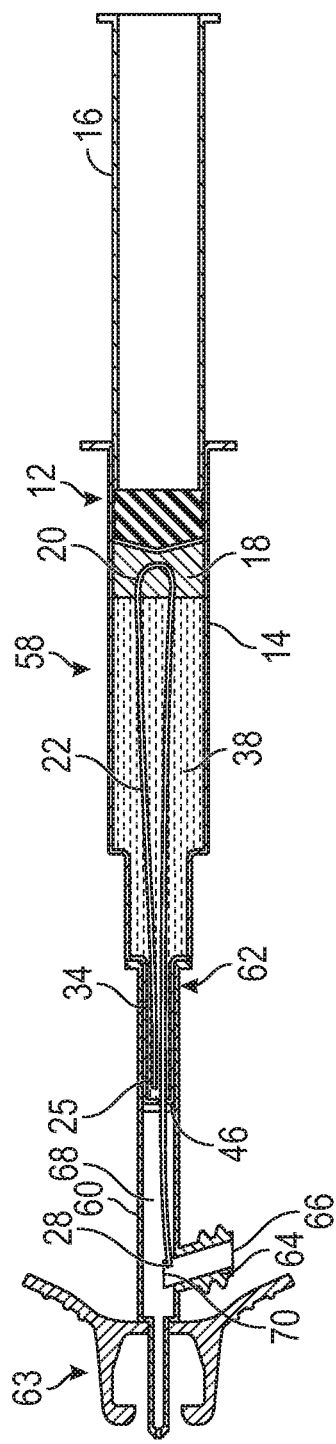
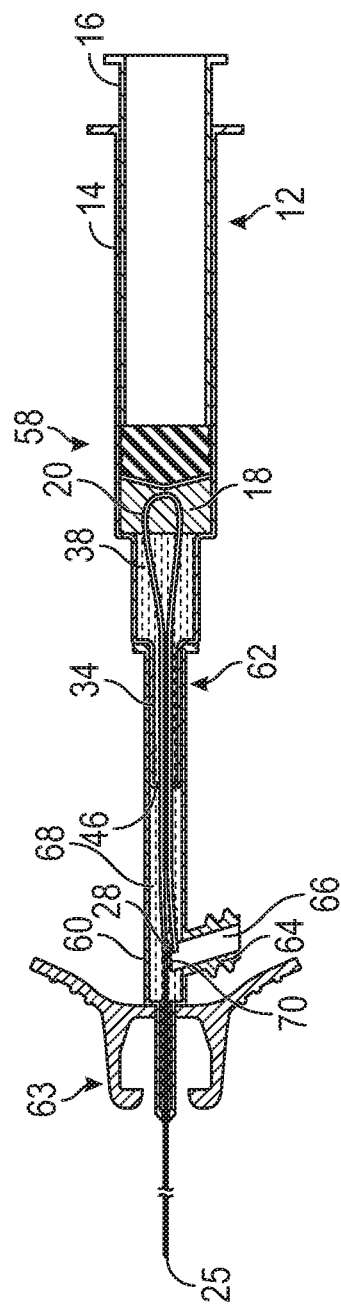
FIG. 4A
FIG. 4B

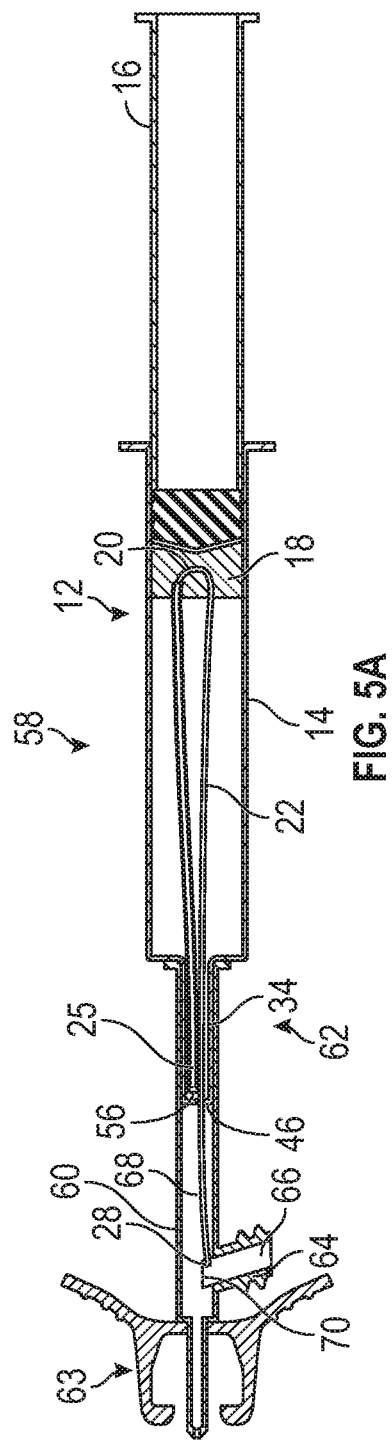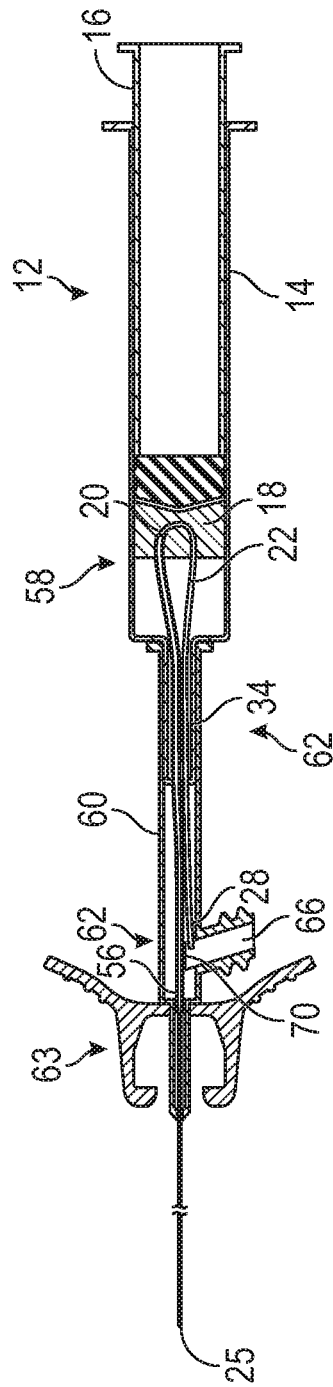

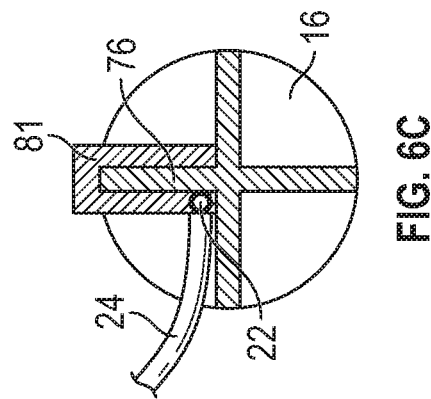
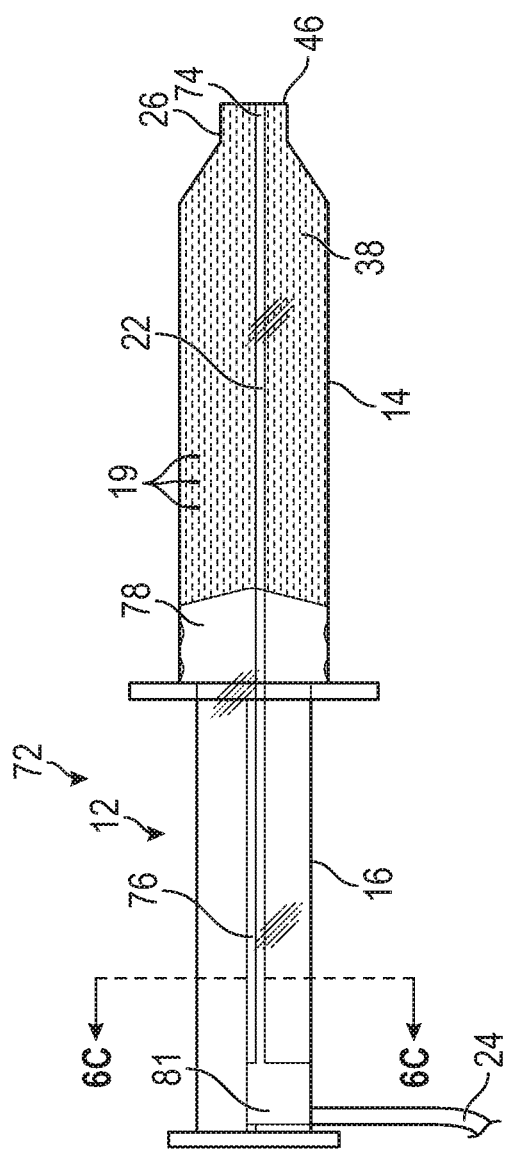
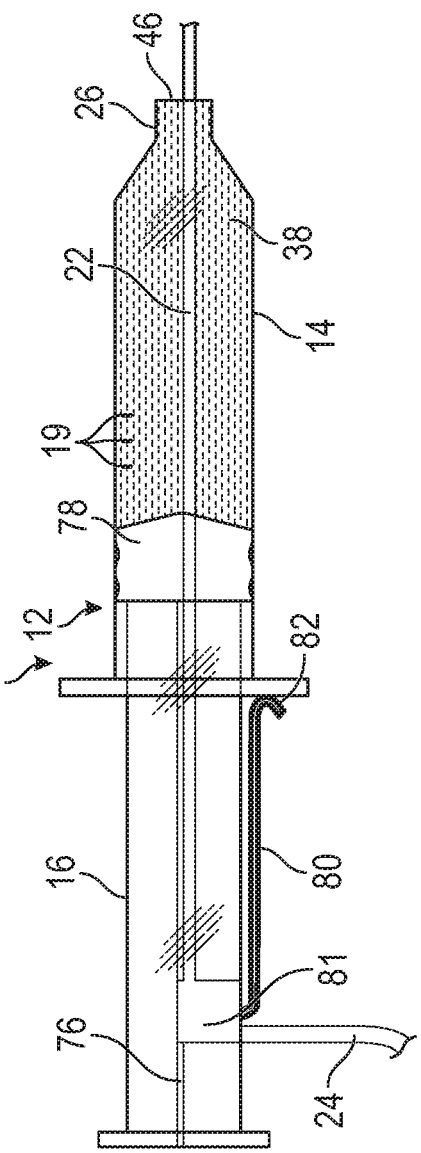

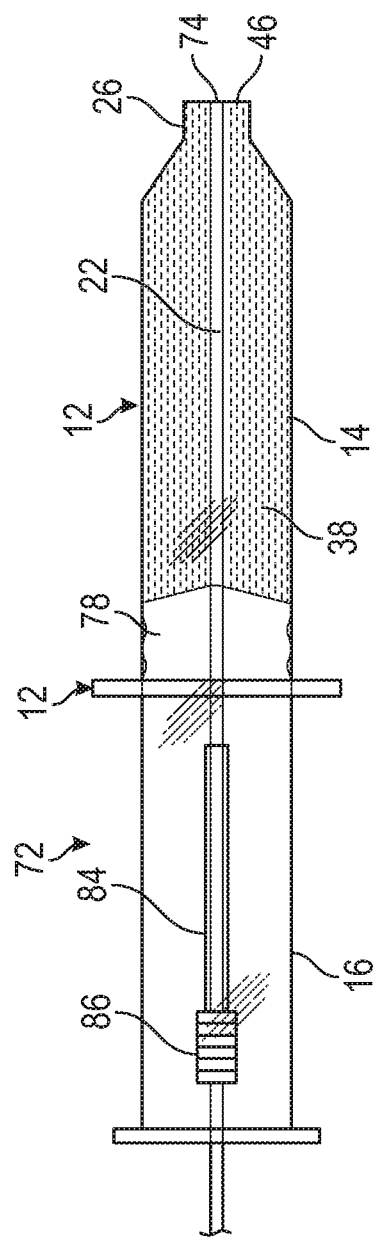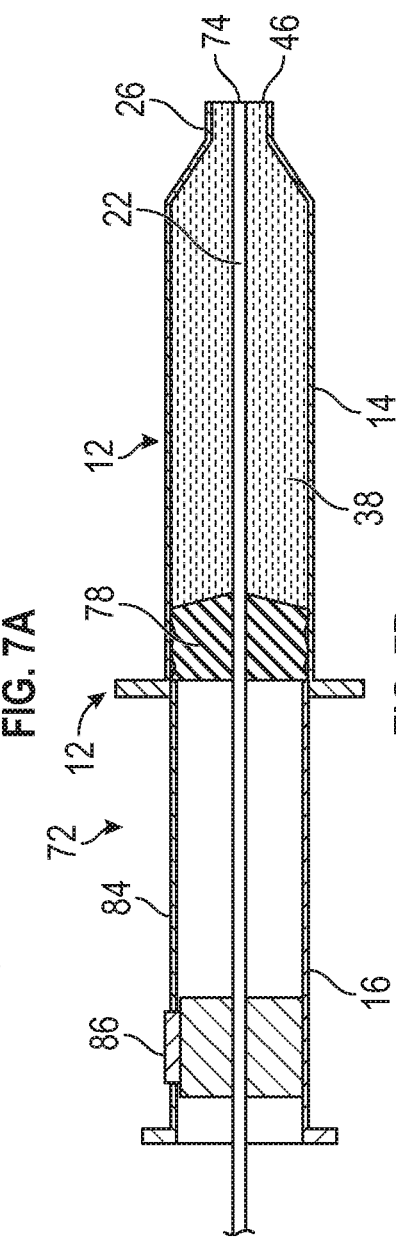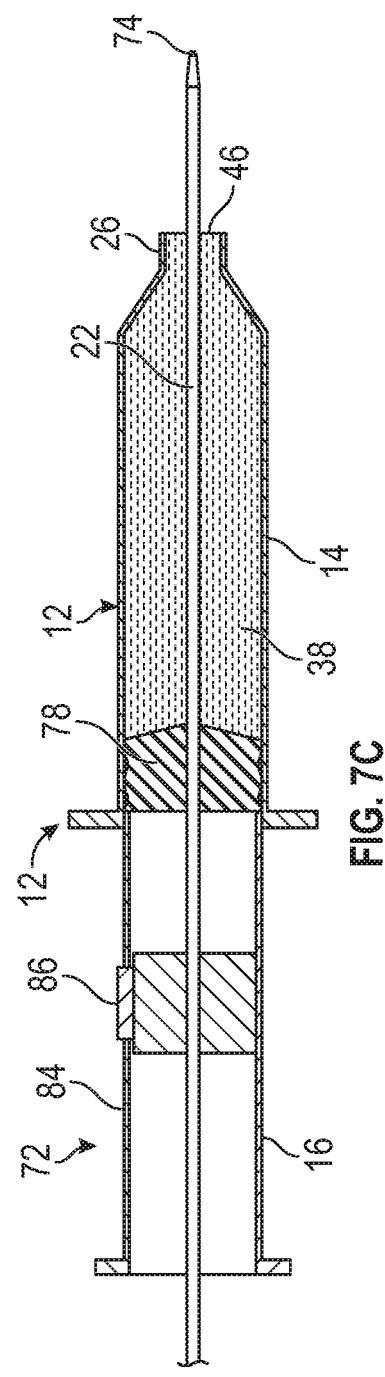

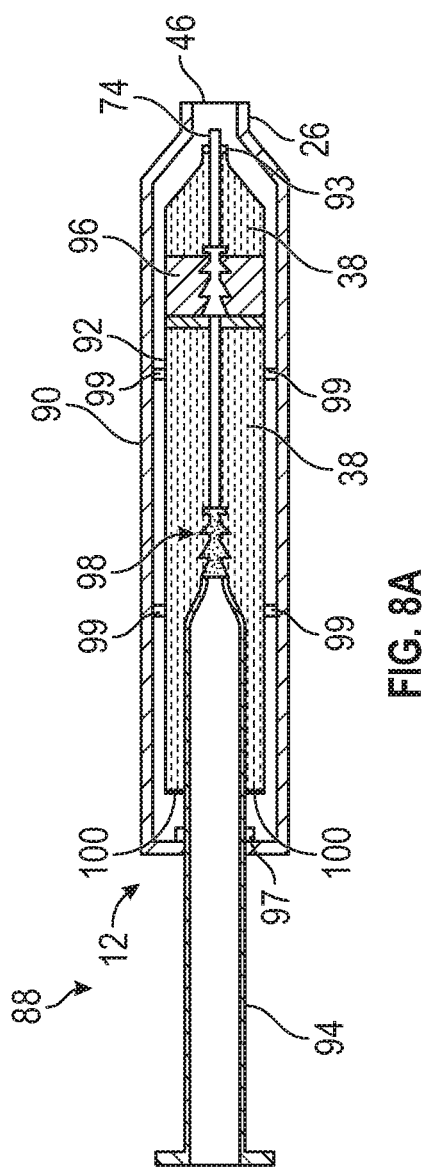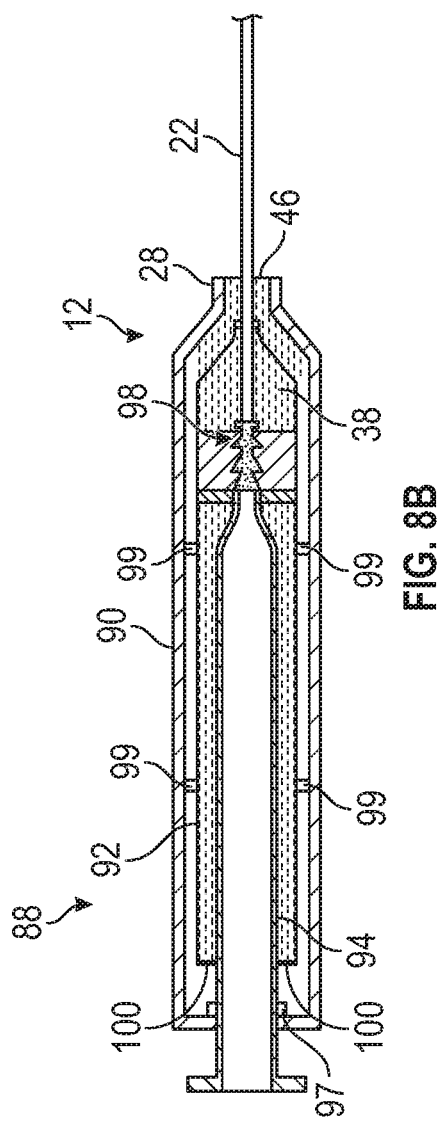
FIG. 8A
FIG. 8B

SYRINGE-BASED DELIVERY DEVICE FOR A VASCULAR ACCESS INSTRUMENT

RELATED APPLICATIONS

This application claims the benefit of U.S. Provisional Application No. 62/773,029, filed Nov. 29, 2018, and entitled SYRINGE-BASED DELIVERY DEVICE FOR A VASCULAR ACCESS INSTRUMENT, which is incorporated herein in its entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral intravenous ("IV") catheter. As its name implies, the over-the-needle catheter may be mounted over an introducer needle having a sharp distal tip. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into vasculature of the patient.

In order to verify proper placement of the introducer needle and/or the catheter in the blood vessel, a clinician generally confirms that there is "flashback" of blood in a flashback chamber of the catheter assembly. Once placement of the needle has been confirmed, the clinician may temporarily occlude flow in the vasculature and remove the needle, leaving the catheter in place for future blood withdrawal or fluid infusion.

Blood withdrawal using a peripheral IV catheter may be difficult for several reasons, particularly when an indwelling time of the catheter is more than one day. For example, when the catheter is left inserted in the patient for a prolonged period of time, the catheter or vein may be more susceptible to narrowing, collapse, kinking, blockage by debris (e.g., fibrin or platelet clots), and adhering of a tip of the catheter to the vasculature. Due to this, catheters may often be used for acquiring a blood sample at a time of catheter placement but are much less frequently used for acquiring a blood sample during the catheter dwell period. Therefore, when a blood sample is required, an additional needle stick is needed to provide vein access for blood collection, which may be painful for the patient and result in higher material costs. Accordingly, there is a need for catheter systems and methods that facilitate placement of blood sample instruments, such as, for example, catheters and probes, in the vasculature of the patient without additional needle sticks.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to a syringe-based delivery device for delivering a vascular access instrument into a catheter assembly and/or vasculature of a patient, as well as related systems and methods. In some embodiments, the delivery device may include a syringe having a barrel and a plunger movable within the barrel. In some embodiments, the delivery device may include a guide feature, which may be disposed within the barrel and/or coupled to the plunger. In some embodiments, the guide feature may be movable with the plunger. In some embodiments, the guide feature may include a channel, which may be generally U-shaped. In some embodiments, the guide feature and channel may be oriented in various ways within the barrel. For example, the channel may be horizontally or vertically oriented within the barrel.

In some embodiments, the delivery device may include an instrument disposed within the barrel and extending through the guide feature. For example, the instrument may extend through the channel. In some embodiments, in response to depression of the plunger or distal movement of the plunger, the guide feature may be moved in the distal direction a first distance, the instrument may move through the channel, and a first end of the instrument may be advanced in the distal direction a second distance, which may be greater than the first distance. In some embodiments, the second distance may be at least two times the first distance.

In some embodiments, the first end of the instrument may be advanced in the distal direction beyond a distal end of the syringe in response to the plunger being partially and/or fully depressed within the barrel in the distal direction. In some embodiments, a second end of the instrument may be fixed. In some embodiments, the second end of the instrument may be fixed within the barrel. In some embodiments, a catheter adapter of the catheter assembly may be coupled to the syringe.

In some embodiments, a needleless connector may be disposed between the syringe and the catheter adapter and may connect the syringe to the catheter adapter. In further detail, in some embodiments, a distal end of the needleless connector may be coupled to the catheter adapter of the catheter assembly, and a proximal end of the needleless connector may be coupled to the syringe. In some embodiments, the distal end of the syringe may include connector, which may be configured to couple to a proximal end of the catheter adapter and/or the needleless connector. In some embodiments, an interface adapter may be disposed between the syringe and the catheter adapter and may connect the syringe to the catheter adapter. In some embodiments, the second end of the instrument may be fixed within the interface adapter.

In some embodiments, the barrel may include a liquid, such as, for example, saline or another suitable flushing liquid. In some embodiments, the liquid may completely fill the barrel. In some embodiments, in response to depression of the plunger, the liquid may exit a distal opening of the syringe. In some embodiments, a diameter of the distal opening of the syringe may be greater than an outer diameter of the instrument. In some embodiments, in response to depression of the plunger, the liquid may flow around the instrument and into and/or through the catheter assembly.

In some embodiments, the barrel may not include the liquid, but the syringe may be used to deliver the instrument to the catheter assembly. In these and other embodiments, the distal opening of the syringe may include a septum to create a seal between the distal opening of the syringe and the instrument, and the barrel or a stopper may include a vent for air escape during when advancing the plunger.

In some embodiments, the instrument may include a probe (which may include a sensor), a light tube for disinfection, or another suitable instrument. In some embodiments, the instrument may include a catheter. In these and other embodiments, the syringe may include extension tubing, which may extend outwardly from a distal portion of the syringe. In some embodiments, the second end of the instrument may be coupled to the extension tubing. In some embodiments, blood collected from the patient may flow from the second end of the instrument into the extension tubing.

In some embodiments, a guidewire may be disposed within the instrument. In some embodiments, in response to depression of the plunger within the barrel in the distal direction, the guidewire and the instrument may move through the channel. In some embodiments, in response to depression of the plunger within the barrel in the distal direction, a first end of the guidewire may be advanced in the distal direction. In some embodiments, in response to depression of the plunger, the guide feature may be moved in the distal direction a first distance, the first end of the guidewire may be advanced in the distal direction a second distance. In some embodiments, the second distance may be greater than the first distance. In some embodiments, the second distance may be at least two times the first distance.

In some embodiments, the first end of the guidewire may be advanced in the distal direction beyond the distal end of the syringe in response to the plunger being partially and/or fully depressed. In some embodiments, the second end of the guidewire may be fixed. For example, the second end of the guidewire may be fixed within the barrel or the interface adapter.

In some embodiments, the delivery device may include support tubing, which may extend from and be coupled to the guide feature. In some embodiments, in response to depression of the plunger, the guide feature may be moved in the distal direction a first distance, the instrument may move through the support tubing, a first end of the instrument may be advanced in the distal direction a second distance, and a first end of the support tubing may be advanced in the distal direction the first distance. In these embodiments, the second distance may be greater than the first distance.

In some embodiments, the delivery device may allow the instrument to access the vasculature of a patient through another vascular access device, such as, for example, a catheter assembly, which may be inserted into the vasculature of the patient. In some embodiments, when the instrument is introduced into the catheter assembly via the delivery device, the instrument may access a fluid pathway of the catheter assembly and/or the instrument may extend through the catheter assembly and access the vasculature of the patient. In some embodiments, the catheter assembly may include the catheter adapter and another catheter, which may extend distally from the catheter adapter. In some embodiments, a proximal end of the other catheter may be secured within the catheter adapter.

In some embodiments, the instrument may be coupled to the plunger and movable along the plunger to an advanced position. In some embodiments, the instrument may extend distally into the barrel. In some embodiments, the distal end of the instrument may be configured to be advanced distal to the distal end of the syringe.

In some embodiments, the plunger may include a rib. In some embodiments, the instrument may be coupled to the rib and movable along the rib. In some embodiments, the plunger may include a slot. In these and other embodiments, the instrument may be disposed within the barrel and coupled to an advancement tab movable along the slot. In some embodiments, the plunger may include the stopper. In some embodiments, in response to the plunger moving to the advanced position, the instrument may move through the stopper.

In some embodiments, the syringe may include an outer barrel, an inner barrel, an elongated body movable within the inner barrel, and a plunger head disposed within the inner barrel. In some embodiments, a distal end of the elongated body may couple to the plunger head. In some embodiments, in response to the coupling of the elongated body to the plunger head, the elongated body and the plunger head may be configured to distally advance together to expel liquid from the inner barrel through the distal opening of the syringe.

In some embodiments, an instrument may extend from the distal end of the elongated body and through the plunger head. In some embodiments, in response to advancement of the elongated body in the distal direction within the inner barrel, the distal end of the instrument may be advanced in the distal direction. In some embodiments, in response to the coupling of the elongated body to the plunger head, the elongated body and the plunger head may be configured to proximally retract together to expel liquid from the inner barrel into the outer barrel.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which:

FIG. 1A is a top view of an example delivery device coupled to an example catheter assembly, illustrating an example plunger of the delivery device in a proximal position, according to some embodiments;

FIG. 1B is a cross-sectional view of the delivery device of FIG. 1A coupled to the catheter assembly of FIG. 1A, illustrating the plunger in the proximal position, according to some embodiments;

FIG. 2A is an upper perspective view of the delivery device of FIG. 1A coupled to the catheter assembly of FIG. 1A, illustrating the plunger in a distal position, according to some embodiments;

FIG. 2B is a cross-sectional view of the delivery device of FIG. 1A coupled to the catheter assembly of FIG. 1A, illustrating the plunger in the distal position, according to some embodiments;

FIG. 3A is a cross-sectional view of the delivery device having example support tubing, illustrating the plunger of the delivery device in the proximal position, according to some embodiments;

FIG. 3B is a cross-sectional view of the delivery device of FIG. 3A, illustrating the plunger in the distal position, according to some embodiments;

FIG. 4A is a cross-sectional view of another delivery device having an example instrument with a fixed end disposed in an example interface adapter, illustrating an example plunger of the delivery device in a proximal position, according to some embodiments;

FIG. 4B is a cross-sectional view of the delivery device of FIG. 4A, illustrating the plunger in a distal position, according to some embodiments;

FIG. 5A is a cross-sectional view of the delivery device of FIG. 4A having example support tubing, illustrating the plunger in the proximal position, according to some embodiments;

FIG. 5B is a cross-sectional view of the delivery device of FIG. 5A, illustrating the plunger in a distal position, according to some embodiments;

FIG. 6A is an upper perspective view of another example delivery device, illustrating an example plunger and an example instrument each in a proximal position, according to some embodiments;

FIG. 6B is an upper perspective view of the delivery device of FIG. 6A having an example positioning feature, illustrating the instrument each in a partially advanced position, according to some embodiments;

FIG. 6C is a cross-sectional view of the delivery device of FIG. 6A along the line 6C-6C of FIG. 6A, according to some embodiments;

FIG. 7A is an upper perspective view of the delivery device of FIG. 6A, illustrating an example alternate instrument advancement mechanism, according to some embodiments;

FIG. 7B is a cross-sectional view of the delivery device of FIG. 7A, according to some embodiments;

FIG. 7C is a cross-sectional view of the delivery device of FIG. 7A, illustrating the instrument in a partially advanced position, according to some embodiments;

FIG. 8A is a cross-sectional view of another example delivery device, illustrating an example elongated body in a proximal position, according to some embodiments;

FIG. 8B is a cross-sectional view of the delivery device of FIG. 8A, illustrating the elongated body advanced distally and coupled to an example plunger head, according to some embodiments;

DESCRIPTION OF EMBODIMENTS

Figure 1C:
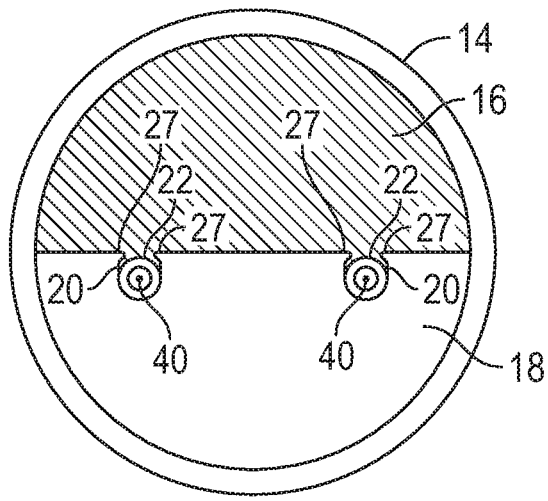
FIG. 1C is a cross-sectional view of the delivery device of FIG. 1A along the line 1C-1C of FIG. 1A, according to some embodiments.

Referring now to FIG. 1A-1B, in some embodiments, a delivery device 10 may include a syringe 12 having a barrel 14 and a plunger 16 movable within the barrel 14. FIGS. 1A-1B illustrate the barrel 14 of the syringe 12 in a proximal position, according to some embodiments. In some embodiments, the delivery device 10 may include a guide feature 18, which may be disposed within the barrel 14 and/or coupled to the plunger 16. In some embodiments, the guide feature 18 may be movable with the plunger 16. In some embodiments, the guide feature 18 may include a channel 20, which may be generally U-shaped. In other embodiments, a portion 17 of the channel 20 may be removed and the channel 20 may include a generally semi-circular shape.

In some embodiments, a distal end of the plunger 16 may include a stopper 21, which may include rubber or another suitable material. In some embodiments, the guide feature 18 may be movable with the plunger 16. For example, the guide feature 18 may be coupled to the stopper 21 and may move proximally and/or distally with the plunger 16. As another example, the stopper 21 may include the guide feature 18, and the guide feature 18 may move proximally and distally with the plunger 16. In further detail, in some embodiments, the channel 20 may be disposed within the stopper 21. In some embodiments, in response to movement of the plunger 16 proximally, the guide feature 18 may be moved proximally and the instrument 22 may be retracted or withdrawn proximally.

In some embodiments, the delivery device 10 may include an instrument 22, which may be disposed within the barrel 14 and may extend through the guide feature 18. For example, the instrument may extend through the channel 20.

In some embodiments, the instrument 22 may include a probe (which may include a sensor), a light tube for disinfection, or another suitable instrument. In some embodiments, the instrument 22 may include a catheter. In these and other embodiments, the syringe 12 may include extension tubing 24, which may extend outwardly from a distal portion of the syringe 12, such as, for example, the barrel 14. In some embodiments, a distal end of the barrel 14 may be proximate the distal connector 34. In some embodiments, the barrel 14 may include a uniform inner diameter.

In some embodiments, a blood collection device 23 may be coupled to the extension tubing 24. In some embodiments, the blood collection device 23 may include a vacuum tube, test tube, or syringe. In some embodiments, the blood collection device may include an adapter, which may be configured to hold a test tube, as illustrated, for example, in FIGS. 1A-1B.

In some embodiments, a first end 25 of the instrument 22 may be advanced in the distal direction beyond a distal opening 46 of the syringe 12 in response to the plunger 16 being partially and/or fully depressed within the barrel 14 in the distal direction. In some embodiments, a second end 28 of the instrument 22 may be fixed. In some embodiments, the second end 28 of the instrument 22 may be fixed within the barrel 14 or the distal connector 34. In some embodiments, the second end 28 of the instrument 22 may be coupled to the extension tubing 24 such that blood collected from the patient via a catheter assembly 30 may flow from the second end 28 of the instrument 22 into the extension tubing 24. In some embodiments, the first end 25 of the instrument 22 may be blunt and/or tapered.

In some embodiments, a catheter adapter 32 of the catheter assembly 30 may be coupled to the syringe 12. In further detail, in some embodiments, a distal end 26 of the syringe 12 may include a distal connector 34, which may be configured to couple to a proximal end of the catheter adapter 32. In some embodiments, the distal connector 34 may include a luer adapter, such as a slip or thread male or female luer adapter, or another suitable connector.

In some embodiments, a needleless connector may connect the syringe 12 to the catheter adapter 32. In further detail, in some embodiments, the distal connector 34 may be configured to couple to a proximal end of the needleless connector. In some embodiments, a distal end of the needleless connector may be coupled to the proximal end of the catheter adapter 32. In some embodiments, the needleless connector may include a luer adapter, such as a male or female luer adapter, or any other suitable connector. In some embodiments, the needleless connector may include a pro re nata ("PRN") connector. In some embodiments, the needleless connector may include a SMARTSITE™ Needle-Free Connector available from Becton, Dickinson and Company, a Q-SYTE™ Luer Activated Split Septum available from Becton, Dickinson and Company, an INTERLINK™ Needlefree System available from Baxter, or another other suitable needleless connector.

In some embodiments, the catheter assembly 30 may include a catheter 36, which may be secured within the catheter adapter 32 and may extend distally from the catheter adapter 32. In some embodiments, the catheter 36 may include a peripheral intravenous catheter, which may be indwelling within vasculature of the patient. In some embodiments, the catheter adapter 32 may be integrated, having an integrated extension tube (not illustrated), or non-integrated.

In some embodiments, the delivery device 10 may allow the instrument 22 to access the vasculature of a patient through the catheter 36, which may be inserted into the vasculature of the patient. In some embodiments, when the instrument 22 is introduced into the catheter assembly via the delivery device 10, the instrument may access a fluid pathway of the catheter assembly 30 and/or the instrument 22 may extend through the catheter assembly 30 and access the vasculature of the patient.

In some embodiments, the catheter assembly 30 may include a needle hub coupled to the proximal end of the catheter adapter 32 and an introducer needle extending distally from the needle hub (not illustrated). In some embodiments, the needle hub and the introducer needle may be removed from the catheter assembly 30 in response to placement of the catheter 36 within vasculature of the patient, and the delivery device 10 may be coupled to the proximal end of the catheter adapter 32 after the needle hub and introducer needle are removed.

In some embodiments, the guide feature 18 and the channel 20 may be oriented in various ways and angles within the barrel 14. For example, the channel 20 may be generally horizontally or vertically oriented within the barrel 14 when the delivery device 10 is coupled with the catheter adapter 32 positioned for insertion into a patient.

In some embodiments, the barrel 14 may include a liquid 38, such as, for example, saline or another suitable flushing liquid. In some embodiments, the liquid 38 may completely fill the barrel 14. In some embodiments, the liquid 38 may be used to flush all or a portion of the catheter assembly 30, as will be explained in further detail.

In some embodiments, a guidewire 40 may be disposed within the instrument 22. In some embodiments, a first end 42 of the guidewire 40 may be advanced in the distal direction beyond the distal end of the syringe 12 in response to the plunger 16 being partially and/or fully depressed. In some embodiments, a second end 44 of the guidewire 40 may be fixed. For example, the second end 44 of the guidewire 40 may be fixed within the barrel 14.

In some embodiments, the guidewire 40 may be used to facilitate placement of the instrument 22 within the vasculature of the patient, which may result in less vein-related trauma. In some embodiments, the guidewire 40 may support the instrument 22, such as a catheter, during advancement to prevent collapse or buckling of the instrument 22 as it advances through a second catheter (such as, for example, the catheter 36, illustrated in FIGS. 1A-1B). In some embodiments, the guidewire 40 may support the instrument 22 along all or a portion of the instrument 22 to improve structural reliability, provide adequate blood collection fill time performance, maintain acceptable blood hemolysis risks, and minimize a risk of kinking of the instrument 22. In some embodiments, the guidewire 40 and the instrument 22 may be enclosed within the delivery device 10 upon completion of blood sampling. It is understood that in some embodiments, the delivery device 10 may not include the guidewire 40.

Referring now to FIG. 1C, in some embodiments, the channel 20 may contact and support the instrument 22. In some embodiments, a shape of the channel 20 may be configured to decrease a risk of kinking or bending of the instrument 22 as the instrument 22 moves through the channel. In some embodiments, an outer diameter of the guidewire 40 may be less than an inner diameter of the instrument 22 such that fluid may easily flow through the instrument 22. In some embodiments, a curvature of the U-shape may vary depending on, for example, on a bend radius of a material from which the instrument 22 is constructed. In some embodiments, the curvature of the U-shape may be configured to prevent kinking of or damage to the instrument 22. In some embodiments, the channel 20 may include one or more protrusions 27, such as, for example, a lip or a detent, which may facilitate securement of the instrument 22 within the channel 20.

Figure 1D:
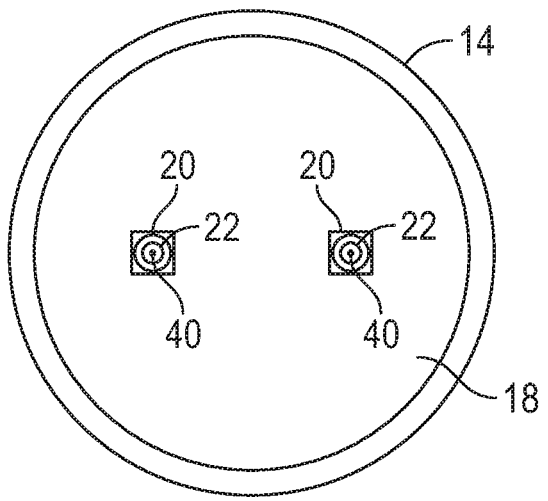
FIG. 1D is another cross-sectional view of the delivery device of FIG. 1A along the line 1C-1C of FIG. 1A, according to some embodiments.

Referring now to FIG. 1D, as an alternative to the guide feature configuration illustrated in FIG. 1C in which the guide feature 18 only partially spans a lumen of the barrel 14, in some embodiments, the guide feature 18 may span an entirety of the lumen of the barrel 14. In further detail, in some embodiments, the guide feature 18 may contact an entirety of an inner surface of the barrel at a cross-section of the barrel, as illustrated, for example, in FIG. 1D.

Figure 1E:
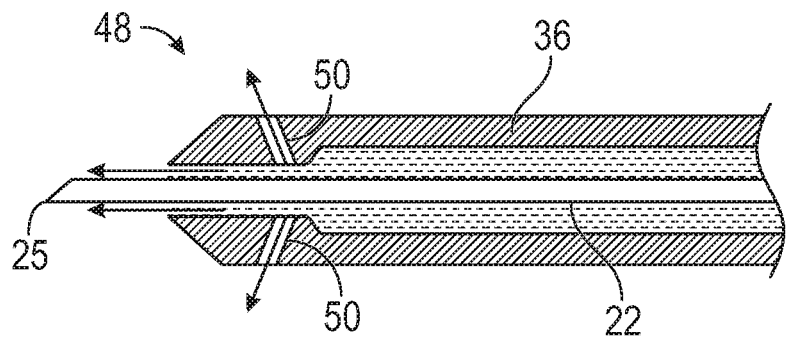
FIG. 1E is a cross-sectional view of a distal end of an example catheter of the catheter assembly of FIG. 1A, according to some embodiments.
Figure 1F:
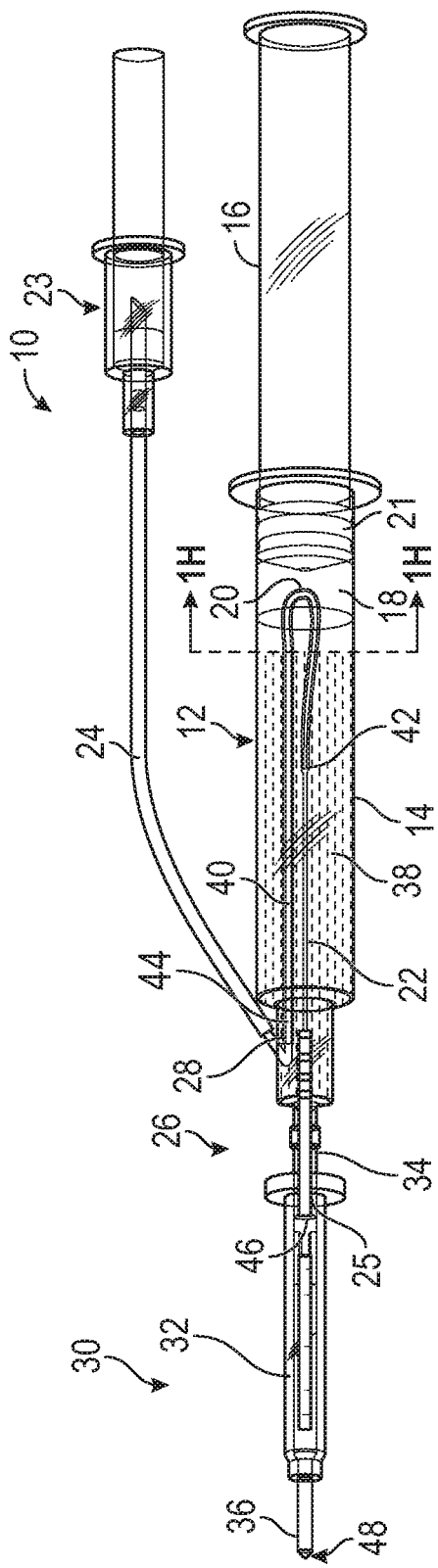
FIG. 1F is a side view of another example delivery device coupled to the catheter assembly, illustrating an example channel vertically oriented within an example barrel, according to some embodiments.
Figure 1G:
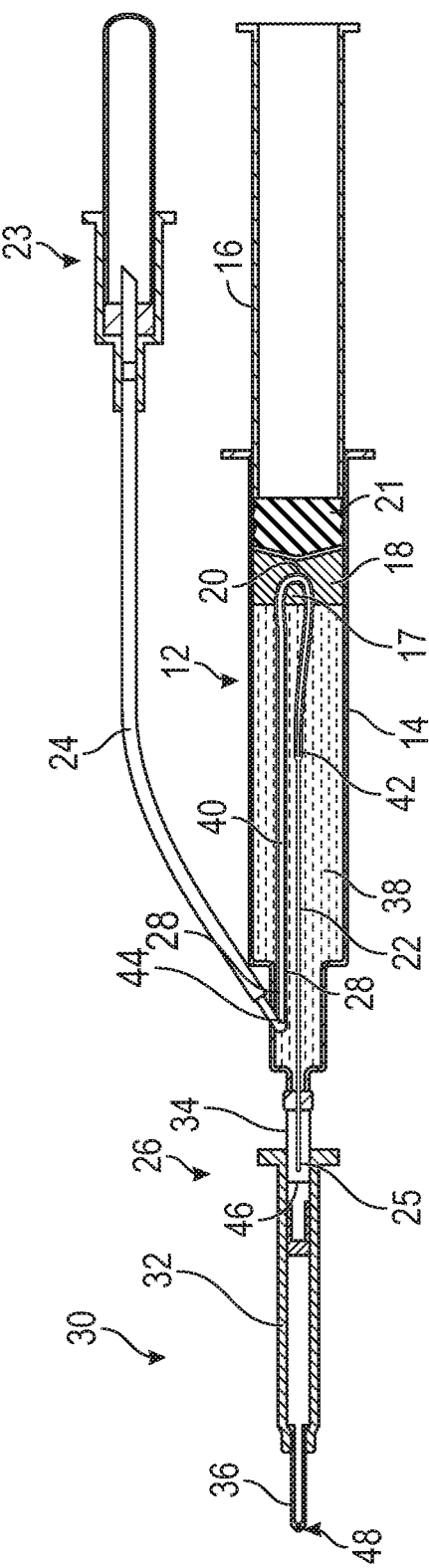
FIG. 1G is a cross-sectional view of the delivery device of FIG. 1F, illustrating the channel vertically oriented within the barrel, according to some embodiments.
Figure 1H:
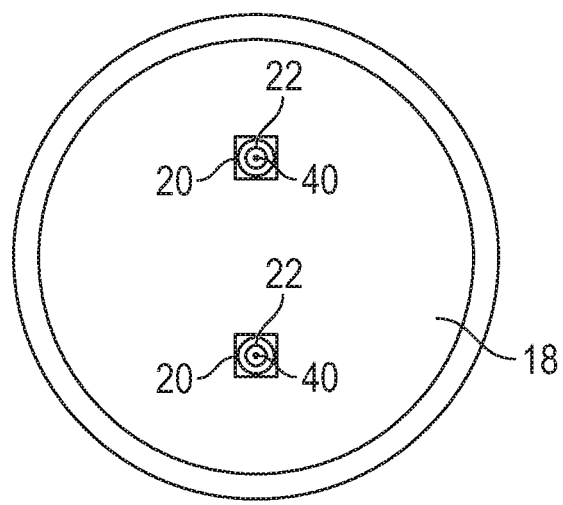
FIG. 1H is a cross-sectional view of the delivery device of FIG. 1F along the line 1H-1H of FIG. 1F, according to some embodiments.
Figure 6D:
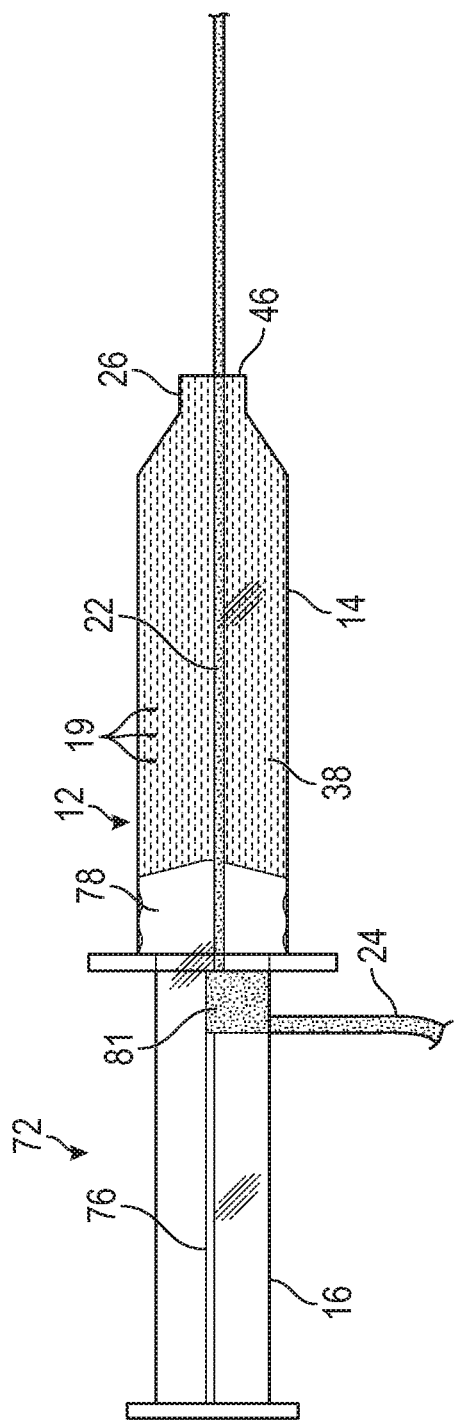
FIG. 6D is an upper perspective view of the delivery device of FIG. 6A, illustrating the instrument in an advanced position, according to some embodiments.
Figure 6E:
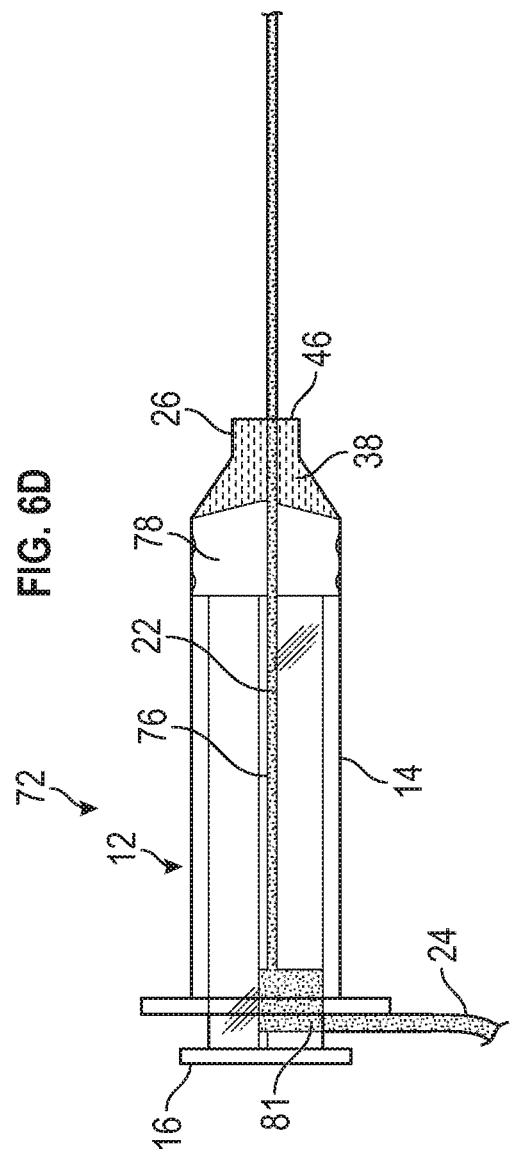
FIG. 6E is an upper perspective view of the delivery device of FIG. 6A, illustrating the instrument and the plunger each in a fully advanced position, according to some embodiments.

Referring now to FIG. 1F-1H, in some embodiments, as opposed to being horizontally oriented, as illustrated, for example, in FIGS. 1A-1B, the channel 20 may be vertically oriented within the syringe 12, as illustrated, for example, in FIGS. 1F-1G. In some embodiments, the guide feature 18 may span an entirety of the lumen of the barrel 14 and contact an entirety of an inner surface of the barrel at a cross-section of the barrel, as illustrated, for example, in FIG. 1H. In other embodiments, the guide feature 18 may only partially span the lumen of the barrel 14.

Referring now to FIG. 2A-2B, in some embodiments, the plunger 16 may be depressed or moved in a distal direction from the proximal position. In some embodiments, in response to depression of the plunger 16, the guide feature 18 may be moved in the distal direction a first distance, the instrument 22 may move through the channel 20, and a first end 25 of the instrument 22 may be advanced in the distal direction a second distance, which may be greater than the first distance. In some embodiments, the second distance may be at least two times the first distance ("a 1:2 advancement ratio") due to the U-shape of the channel 20. In some embodiments, the delivery device 10 and the 1:2 advancement ratio (or another advancement ratio where the second distance is greater than the first distance) between the guide feature 18 and the first end 25 of the instrument 22 may provide reliability and structural support as the instrument 22 is distally advanced, while also providing an instrument 22 with long reach.

In some embodiments, in response to depression of the plunger 16, the liquid 38 may exit the distal opening 46 of the syringe 12. In some embodiments, a diameter of the distal opening 46 of the syringe 12 may be greater than an outer diameter of the instrument 22. In some embodiments, in response to depression of the plunger 16, the liquid 38 may flow around the instrument 22 and into and/or through the catheter assembly 30.

In some embodiments, the instrument 22 may include the guidewire 40 and/or a multi-diameter catheter, such as described, for example, in U.S. Patent Application No. 62/660,646, filed Apr. 20, 2018, entitled "MULTI-DIAMETER CATHETER AND RELATED DEVICES AND METHODS," which is incorporated herein by reference. In some embodiments, the multi-diameter catheter may allow improved blood flow rates during blood collection. In some embodiments, the distal end of the guidewire 40 may be disposed proximal to a transition of the multi-diameter catheter to allow fluid to flow in an annular space between an outer surface of the guidewire 40 and an inner surface of the multi-diameter catheter.

In some embodiments, in response to depression of the plunger 16 within the barrel 14 in the distal direction, the guidewire 40 may move through the channel 20 within the instrument 22, and the first end 42 of the guidewire 40 may be advanced in the distal direction. In some embodiments, in response to depression of the plunger 16, the guide feature 18 may be moved in the distal direction a first distance, the first end 42 of the guidewire 40 may be advanced in the distal direction a second distance. In some embodiments, the second distance may be greater than the first distance. In some embodiments, the second distance may be at least two times the first distance.

Referring back to FIG. 1E, in some embodiments, a distal end 48 of the catheter 36 may include one or more flow holes 50 extending through a wall of the catheter 36. In some embodiments, the liquid 38 may flow out of the flow holes 50 in response to depression of the plunger 16.

Referring now to FIGS. 3A-3B, in some embodiments, the delivery device 10 may include support tubing 54, which may extend from the guide feature 18. In some embodiments, the support tubing 54 may be secured to the guide feature 18. In some embodiments, in response to depression of the plunger 16, the guide feature 18 may be moved in the distal direction a first distance, the instrument 22 may move through the support tubing 54, and a first end 56 of the support tubing 54 may be advanced in the distal direction the first distance. In some embodiments, the support tubing 54 may include a uniform inner diameter and/or uniform outer diameter along all or a portion of a length of the support tubing 54.

In some embodiments, when the delivery device 10 includes the support tubing 54, the instrument 22 may include a catheter constructed of a softer material than polyimide, which may be less damaging to the vein wall. In these and other embodiments, the instrument 22 may include a tube constructed of one or more of polyurethane, silicon, thermoplastic elastomer ("TPE"), thermoplastic polyurethane ("TPU"), and another suitable compliant material.

In some embodiments, the support tubing 54 may include a larger inner diameter than an outer diameter of the instrument 22 such that the instrument 22 may easily move through the support tubing 54. In some embodiments, the support tubing 54 may provide support to the first end 25 or the free end of the instrument 22. In some embodiments, in response to depression of the plunger 16 and movement of the guide feature 18 the first distance, the first end 56 of the support tubing 54 may be advanced in the distal direction a distance equal to the first distance (a "1:1 advancement ratio"), while the first end 25 of the instrument 22 may be advanced a distance greater than that of the first distance, such as for example, twice the first distance ("a 1:2 advancement ratio"). In some embodiments, the differing advancement ratios of the guide feature 18 with respect to the first end 25 and the guide feature 18 with respect to the support tubing 54 may result in the support tubing 54 not advancing distally beyond a portion of the instrument 22, and the portion of the instrument 22 advancing distally through the catheter assembly 30 and into the vasculature. In these and other embodiments, the portion of the instrument 22 may have a decreased outer diameter or the instrument 22 may include a uniform diameter along all or a portion of a length of the instrument 22.

In some embodiments, given the 1:2 advancement ratio (or another advancement ratio where the second distance is greater than the first distance) between the guide feature 18 and the first end 25 of the instrument 22 and the 1:1 advancement ratio between the guide feature 18 and the first end 56 of the support tubing 54, the first end 25 of the instrument 22 may exit the first end 56 of the support tubing 54. In some embodiments, the first end 25 of the instrument 22 may exit the first end 56 of the support tubing 54 to facilitate entry of the instrument 22 into a portion of the catheter assembly 30 that may be too narrow for the support tubing 54 to enter.

In some embodiments, the delivery device 10 may facilitate a timed or delayed exit of the instrument 22 from the support tubing 54. In further detail, in some embodiments, the first end 25 of the instrument 22 may be shortened so that it is positioned even with or proximal to the first end 56 of the support tubing 54 when the guide feature 18 is fully retracted, as illustrated, for example, in FIG. 3A.

Referring now to FIGS. 4A-4B, another delivery device 58 is illustrated, according to some embodiments. In some embodiments, the delivery device 58 may include or correspond to the delivery device 10, discussed with respect to FIGS. 1-3. In further detail, in some embodiments, the delivery device 58 may include one or more features of the delivery device 10 and/or the delivery device 10 may include one or more features of the delivery device 58.

In some embodiments, the second end 28 of the instrument 22 may be fixed within an interface adapter 60, which may connect the delivery device 58 to a proximal end of the needleless connector or a proximal end of a catheter adapter, such as, for example, the catheter adapter 32 discussed with respect to FIGS. 1-3. In some embodiments, the needleless connector may be disposed between the interface adapter 60 and the catheter adapter and may connect the interface adapter 60 to the catheter adapter. In some embodiments, a proximal end 62 of the interface adapter 60 may be configured to couple with the distal connector 34 of the delivery device 58. In some embodiments, the proximal end 62 may include a luer adapter, such as a slip or thread male or female luer adapter, or another suitable connector. In some embodiments, the proximal end 62 of the interface adapter 60 may be removably or non-removably coupled to the distal connector 34. In some embodiments, a distal end 63 of the interface adapter 60 may include a luer adapter, such as a slip or thread male or female luer adapter, or another suitable connector, which may be configured to couple the proximal end of the needleless connector or the proximal end of the catheter adapter.

In some embodiments, the interface adapter 60 may include a side port 64, which may include a luer adapter, such as a slip or thread male or female luer adapter, or another suitable connector. In some embodiments, the delivery device 58 may include a first cap and/or a second cap (not illustrated). The first cap may be coupled to and seal the distal opening 46 of the syringe 12 in some embodiments where the instrument 22 is fully contained within the syringe 12 when the plunger 16 is in the proximal position. The first cap may be coupled to and seal the distal end of the interface adapter 60 in some embodiments where the first end of the instrument 22 is fixed within the interface adapter 60. In some embodiments, the second cap may seal the side port 64. In some embodiments, the first cap may be removable to allow connection of the delivery device 58 to the interface adapter 60 and/or the second cap may be removable to allow coupling of a blood collection device to the side port 64, for example.

In some embodiments, the blood collection device, such as, for example, the blood collection device 23 of FIGS. 1A-1B and 2A-2B, may be coupled to the luer adapter of the side port 64 to collect blood from the patient. In some embodiments, the blood collection device may include a syringe, a blood collection tube, or another suitable device. In embodiments, extension tubing 24 may be coupled to the side port 64 and may extend from the side port 64. In some embodiments, a proximal end of the extension tubing 24 may be coupled to the blood collection device.

In some embodiments, the side port 64 may include a cavity 66 that may be sealed off from a lumen 68 of the interface adapter 60, which may prevent blood or other fluid from leaking into the lumen 68. In some embodiments, the cavity 66 may be sealed off from the lumen 68 by a wall 70, through which the second end 28 of the instrument 22 and/or the second end 44 of the guidewire 40 (not illustrated in FIGS. 4A-4B) may extend. In some embodiments, the guidewire 40, illustrated, for example, in FIGS. 1A-1C and 2A-2B, may be disposed within the instrument 22 and may operate in a similar fashion as discussed with respect to FIGS. 1A-1C and 2A-2B.

Referring now to FIGS. 5A-5B, in some embodiments, the delivery device 58 may include the support tubing 54, which may extend from the guide feature 18. In some embodiments, the support tubing 54 may be secured to the guide feature 18. In some embodiments, in response to depression of the plunger 16, as illustrated, for example, in FIG. 5B, the guide feature 18 may be moved in the distal direction a first distance, the instrument 22 may move through the support tubing 54, and a first end 56 of the support tubing 54 may be advanced in the distal direction the first distance. In some embodiments, the support tubing 54 may include a uniform inner diameter and/or uniform outer diameter along all of a portion of a length of the support tubing 54.

Referring now to FIGS. 6A-6E, another example delivery device 72 is illustrated, according to some embodiments. In some embodiments, the delivery device 72 may include or correspond to the delivery device 10, discussed with respect to FIGS. 1-3, and/or the delivery device 58, discussed with respect to FIGS. 4-5. In further detail, in some embodiments, the delivery device 72 may include one or more features of the delivery device 10 and/or the delivery device 58. In some embodiments, the delivery device 10 and/or the delivery device 58 may include one or more features of the delivery device 72.

In some embodiments, the instrument 22 may be coupled to the plunger 16 and may be movable along the plunger 16 in the distal direction to an advanced position. In some embodiments, the instrument 22 may also be moved proximally along the plunger 16 to retract the instrument 22. In these and other embodiments, the instrument 22 may move independently of the plunger. In some embodiments, the instrument 22 may extend distally into the barrel 14. In some embodiments, a distal end 74 of the instrument 22 may be configured to be advanced distal to the distal opening 46 of the syringe 12, as illustrated, for example in FIGS. 6D-6E.

In some embodiments, the plunger 16 may include at least one rib 76. In some embodiments, the instrument 22 may be coupled to the rib 76 and movable along the rib 76. In some embodiments, the instrument 22 may be coupled to the rib 76 via an advancement tab 81, which may extend over the rib 76, as illustrated in FIG. 6C, for example. In some embodiments, the plunger 16 may include a stopper 78, which may include rubber or another suitable material. In some embodiments, in response to the plunger 16 moving to the advanced position, the instrument 22 may move through the stopper 78.

As illustrated in FIG. 6B, in some embodiments, a positioning feature 80 may include a proximal end coupled to the advancement tab 81, which may be coupled to the instrument 22 and configured to move the instrument 22 proximally and/or distally. In some embodiments, the positioning feature 80 may be rigid. In some embodiments, a distal end 82 of the positioning feature 80 may contact an upper surface of the syringe 12 to prevent distal movement of the advancement tab 81 and the instrument 22. In some embodiments, the distal end 82 of the positioning feature 80 may be free floating, and may contact the upper surface of the syringe 12 in response to movement of the advancement tab 81 and the instrument 22 in the distal direction. In some embodiments, the distal end 82 of the positioning feature 80 may be attached or selectively attached to the syringe 12. In some embodiments, the positioning feature 80 may secure a position of the instrument 22 when the delivery device 72 is packaged and/or prior to use.

In some embodiments, in response to depression of the plunger 16, the liquid 38 may flow out of the distal opening 46 of the syringe 12. In some embodiments, the distal end 26 of the syringe 12 may include a luer adapter, such as a slip or thread male or female luer adapter, or another suitable connector. In some embodiments, the syringe 12 may be coupled to a proximal end of the catheter adapter 32 of the catheter assembly 30 (illustrated, for example, in FIGS. 1A-1B and 2A-2B), and the instrument 22 may be advanced in the distal direction such that the instrument 22 is disposed in a fluid pathway of the catheter assembly 30 and/or advanced beyond the distal end 48 of the catheter 36.

In some embodiments, a method of operating the delivery device 72 may include coupling the delivery device 72 to the proximal end of the catheter adapter 32, which may include an indwelling catheter 36. In some embodiments, the instrument 22 may then be advanced in the distal direction. In some embodiments, the plunger 16 may be depressed such that the liquid 38 flows around the instrument 22 and through the catheter 36 to flush the catheter 36 and the catheter assembly 30.

In some embodiments, the barrel 14 and/or the plunger 16 may include one or more markings 19, which may provide a visual and/or tactile indication to the user of a position of the instrument. In further detail, in some embodiments, the markings 19 may indicate a distance that the instrument 22 is advanced and/or retracted. In some embodiments, the barrel 14 and/or the plunger 16 may be transparent. It is understood that the barrel 14 and/or the plunger 16 of other embodiments may include the markings.

Referring now to FIGS. 7A-7C, in some embodiments, the plunger 16 of the delivery device 72 may include a slot 84. In these and other embodiments, the instrument 22 may be disposed within the barrel 14 and coupled to an advancement tab 86 movable along the slot 84. In some embodiments, the advancement tab 86 may be coupled to the instrument 22 and configured to move the instrument 22 proximally and/or distally.

Referring now to FIGS. 8A-8E, another example delivery device 88 is illustrated, according to some embodiments. In some embodiments, the delivery device 88 may include or correspond to one or more of the following: the delivery device 10, discussed with respect to FIGS. 1-3; the delivery device 58, discussed with respect to FIGS. 4-5; and the delivery device 72, discussed with respect to FIGS. 6-7. In further detail, in some embodiments, the delivery device 88 may include one or more features of one or more of the following: the delivery device 10, the delivery device 58, and the delivery device 72. In some embodiments, one or more of the following may include one or more features of the delivery device 88: the delivery device 10, the delivery device 58, and the delivery device 72.

In some embodiments, the syringe 12 may include an outer barrel 90, an inner barrel 92, an elongated body 94 movable within the inner barrel 92, and a plunger head 96 disposed within the inner barrel 92. In some embodiments, the elongated body 94 may be advanced from a proximal position, illustrated, for example, in FIG. 8A, in a distal direction, and a distal end 98 of the elongated body 94 may couple to the plunger head 96, as illustrated, for example, in FIG. 8B. In some embodiments, in response to the elongated body 94 being advanced from the proximal position in the distal direction to couple to the plunger head 96, some of the liquid 38 may be expelled from the inner barrel 92. In some embodiments, in response to the coupling of the elongated body 94 to the plunger head 96, the elongated body 94 and the plunger head 96 may be configured to distally advance together to expel the liquid 38 from the inner barrel 92 through the distal opening 46 of the syringe 12, as illustrated, for example, in FIG. 8C. In some embodiments, when the elongated body 94 and the plunger head 96 are coupled together they may form a unitary plunger 16.

In some embodiments, the instrument 22 may extend from the distal end 98 of the elongated body 94 and through the plunger head 96. In some embodiments, in response to advancement of the elongated body 94 in the distal direction within the inner barrel 92, the distal end 74 of the instrument 22 may be advanced in the distal direction. In some embodiments, in response to the coupling of the elongated body 94 to the plunger head 96, the elongated body 94 and the plunger head 96 may be configured to proximally retract together to expel the liquid 38 from the inner barrel 92 into the outer barrel 90, as illustrated, for example, in FIG. 8D. In some embodiments, the elongated body 94 may be coupled to the plunger head 96 in various ways, such as, for example, a snap-fit, an interference fit, threading, a barbed fitting, etc. FIGS. 8A-8D illustrate a barbed fitting, for example.

In some embodiments, one or more one-way valves 100 may be disposed between the inner barrel 92 and the outer barrel 90, and the liquid 38 may flow through the one-way valves from the inner barrel 92 to the outer barrel 90 in response to retraction of the elongated body 94 and the plunger head 96 coupled together. In some embodiments, a distal end of the inner barrel 92 and/or a distal end of the outer barrel 90 may include a septum 93. In some embodiments, the delivery device 88 may include a venting element to prevent a vacuum from being formed as the plunger is retracted proximally. In some embodiments, the venting element may provide venting to a portion of the inner barrel 92 distal to the plunger head 96 and may prevent a vacuum from being formed as the elongated body 94 and the plunger head 96 are retracted proximally.

In some embodiments, a proximal end of the outer barrel 90 may include a seal 97 proximate an opening in the outer barrel 90 through which the elongated body 94 may extend. In some embodiments, the seal 97 may prevent fluid leakage from the proximal end of the outer barrel 90.

In some embodiments, the outer barrel 90 may include multiple pieces, which may be coupled together. In further detail, in some embodiments, the outer barrel 90 may include a first piece and a second piece, which may be coupled together via welding, adhesive, pins, a press-fit, or another suitable means. In some embodiments, the outer barrel 90 may be monolithically formed as a single unit.

In some embodiments, the inner barrel 92 may be fixed within the outer barrel 90 via one or more retaining features. In further detail, in some embodiments, one or more retaining features of the inner barrel 92 may be engaged in a mechanical fit (such as, for example, a snap fit, a press fit, or another suitable fit) with one or more retaining features of the outer barrel 90. In some embodiments, the retaining features may include ribs 99 that may extend from the inner barrel 92 to the outer barrel 90. Example ribs 99 are illustrated in FIGS. 8A-8D. In some embodiments, the ribs 99 may be rigid or semi-rigid. In some embodiments, the retaining features may be annular and may extend around a circumference of the inner barrel 92. In these and other embodiments, the retaining features may include apertures and/or valves which may open in response to fluid pressure, allowing fluid to pass. In some embodiments, fluid may flow around the retaining features.

Figure 8C:
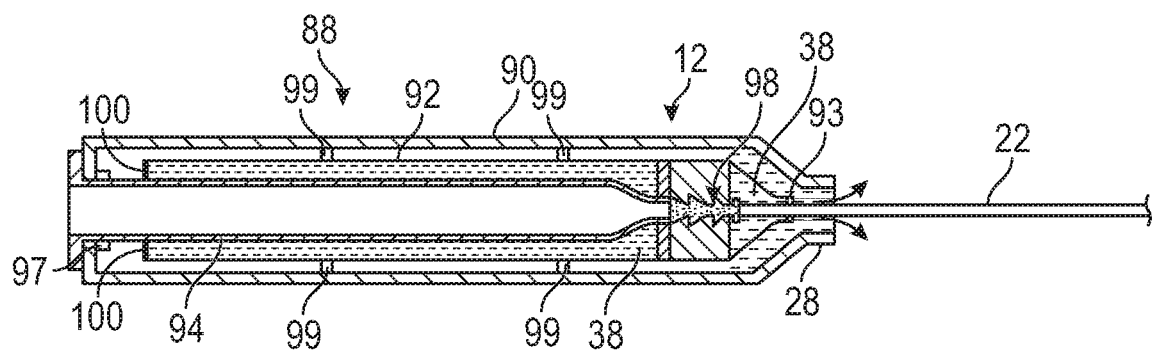
FIG. 8C is a cross-sectional view of the delivery device of FIG. 8A, illustrating the elongated body coupled to the plunger head, and the elongated body and the plunger head advanced distally, according to some embodiments.
Figure 8D:
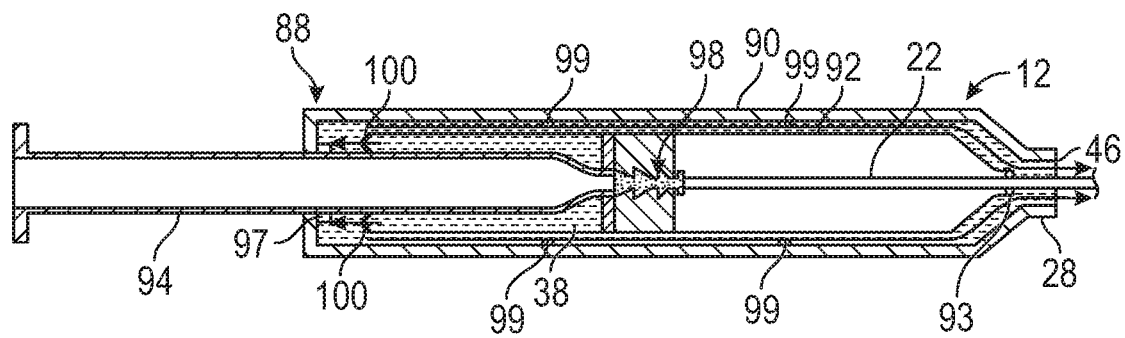
FIG. 8D is a cross-sectional view of the delivery device of FIG. 8A, illustrating the elongated body coupled to the plunger head, and the elongated body and the plunger head retracted proximally, according to some embodiments.
Figure 8E:
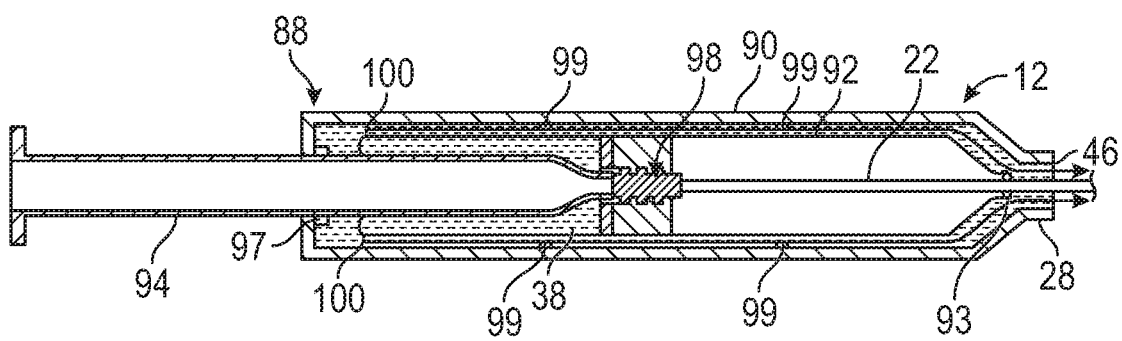
FIG. 8E is another cross-sectional view of the delivery device of FIG. 8A, illustrating the elongated body coupled to the plunger head, and the elongated body and the plunger head retracted proximally, according to some embodiments.

As mentioned, in some embodiments, the elongated body 94 may be coupled to the plunger head 96 in various ways, such as, for example, a snap-fit, an interference fit, threading, a barbed fitting, etc. FIG. 8E illustrates each of the elongated body 94 and the plunger head 96 including one or more threads, according to some embodiments. In some embodiments, the elongated body 94 is threaded to the plunger head 96. In some embodiments, after the user threads the elongated body 94 to the plunger head 96, the elongated body 94 and the plunger head 96 may be distally advanced together to expel the liquid 38 from the inner barrel 92 through the distal opening 46 of the syringe 12 and advance the instrument 22. In some embodiments, in response to the threading of the elongated body 94 to the plunger head 96, the elongated body 94 and the plunger head 96 may be configured to proximally retract together to expel the liquid 38 from the inner barrel 92 into the outer barrel 90 and retract the instrument 22. In some embodiments, in response to the elongated body 94 and the plunger head 96 being partially or fully retracted in the proximal direction, the user may unthread the elongated body 94 may be unthreaded from the plunger head 96 such that the elongated body 94 and the instrument 22 may be removed from the delivery device 88.

Figure 9A:
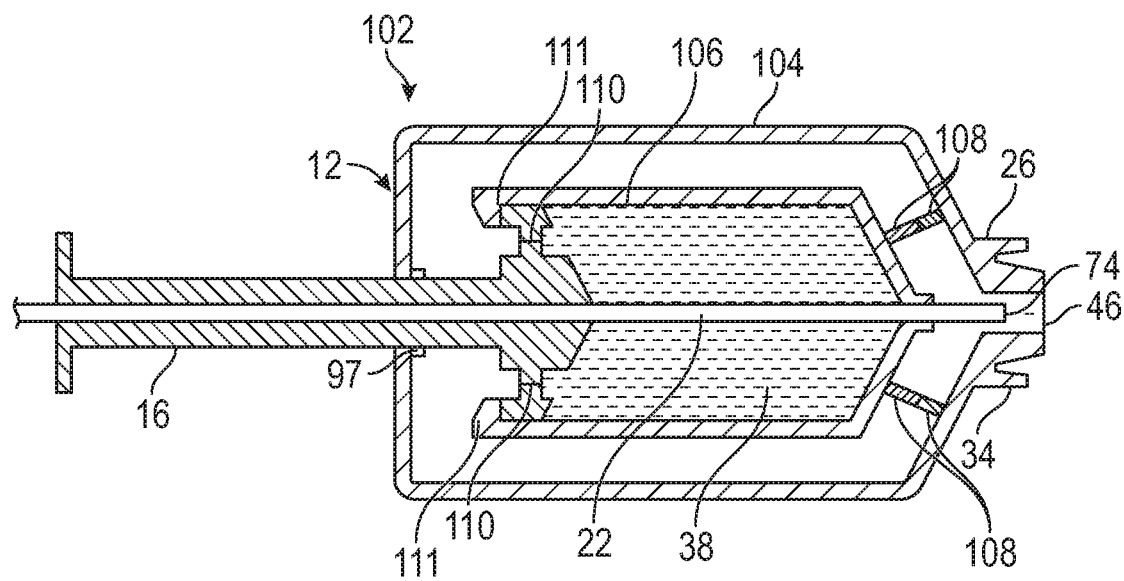
FIG. 9A is a cross-sectional view of another example delivery device, illustrating an example plunger in an initial position, according to some embodiments.
Figure 9B:
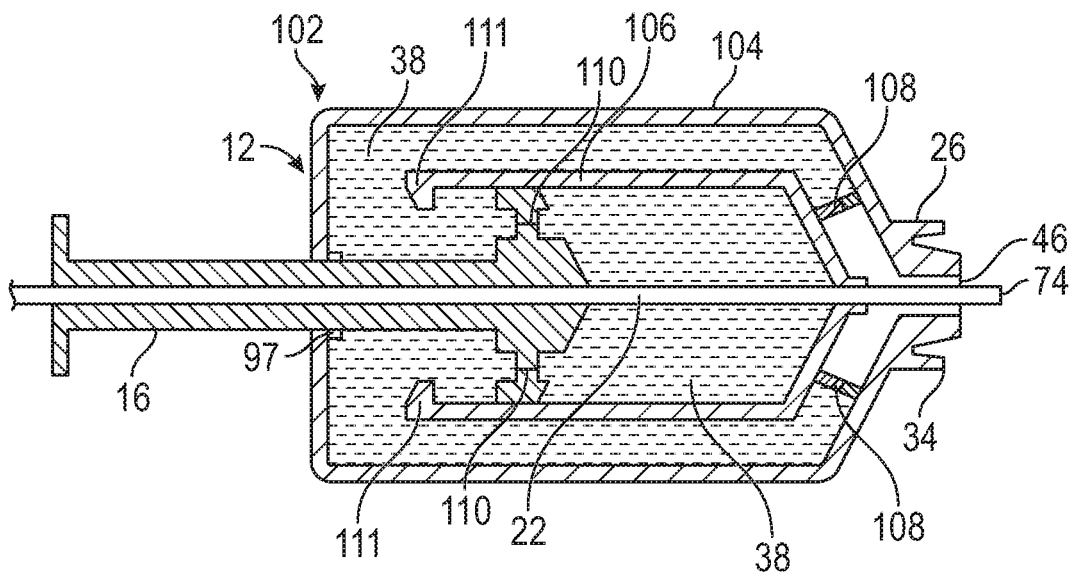
FIG. 9B is a cross-sectional view of the delivery device of FIG. 9A, illustrating the plunger in a partially advanced position, according to some embodiments.
Figure 9C:
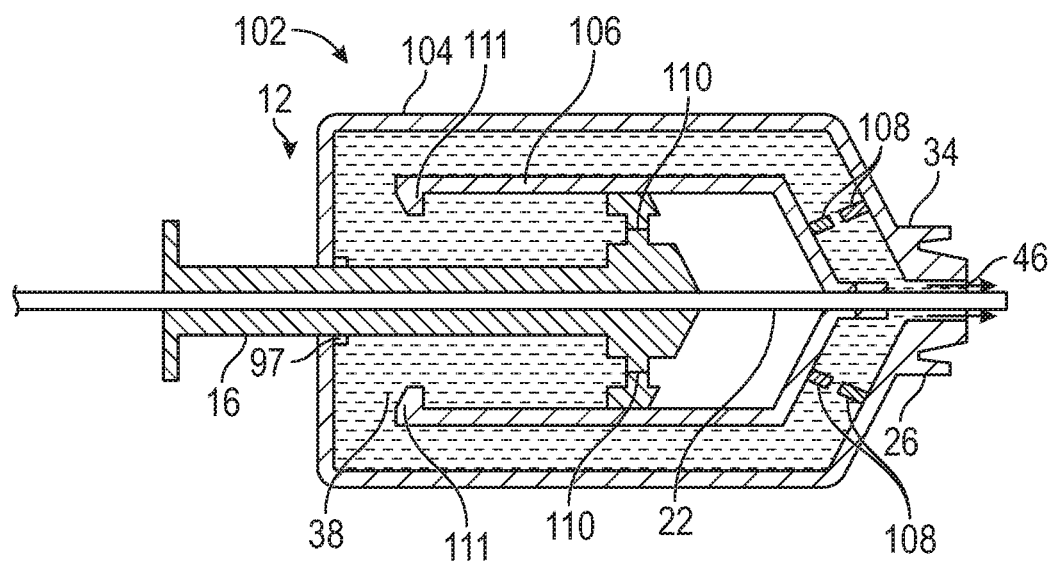
FIG. 9C is a cross-sectional view of the delivery device of FIG. 9A, illustrating the plunger in a partially retracted position, according to some embodiments.

Referring now to FIGS. 9A-9C, another delivery device 102 is illustrated, according to some embodiments. In some embodiments, the delivery device 102 may include or correspond to one or more of the following: the delivery device 10, discussed with respect to FIGS. 1-3; the delivery device 58, discussed with respect to FIGS. 4-5; the delivery device 72, discussed with respect to FIGS. 6-7; and the delivery device 88, discussed with respect to FIG. 8. In further detail, in some embodiments, the delivery device 102 may include one or more features of one or more of the following: the delivery device 10, the delivery device 58, the delivery device 72, and the delivery device 88. In some embodiments, one or more of the following may include one or more features of the delivery device 102: the delivery device 10, the delivery device 58, the delivery device 72, and the delivery device 88.

In some embodiments, the syringe 12 of the delivery device 102 may include an outer barrel 104, an inner barrel 106 containing the liquid 38 and movable within the outer barrel 104 between a proximal position and a distal position, a plunger 16 depressible within the inner barrel 106, and a first valve 108 disposed between the outer barrel 104 and the inner barrel 106. In some embodiments, the inner barrel 106 may be pre-filled with the liquid 38, as illustrated, for example, in FIG. 9A. FIG. 9A illustrates the delivery device 102 in an initial position, or upon removing the delivery device 102 from a package, according to some embodiments.

In some embodiments, the plunger 16 may include a second valve 110 configured to allow the liquid 38 to flow from the inner barrel 106 to the outer barrel 104 in a distal direction in response to depression of the plunger 16 within the inner barrel 106, as illustrated, for example, in FIG. 9B.

In some embodiments, the first valve 108 may be closed when the inner barrel 106 is in the distal position and during depression of the plunger 16, as illustrated, for example, in FIG. 9B. In some embodiments, in response to retraction of the plunger 16 in a proximal direction, the first valve 108 may open and the liquid 38 may flow through the distal opening 46 of the syringe 12, as illustrated, for example, in FIG. 9C. In some embodiments, the delivery device 102 may include multiple first valves 108 and/or multiple second valves 110, as illustrated, for example in FIG. 9A.

In some embodiments, the instrument 22 may extend through the plunger 16. In some embodiments, in response to the depression of the plunger 16, the distal end 74 of the instrument 22 may be advanced in a distal direction. In some embodiments, the distal end 26 of the syringe 12 may include a distal connector 34, such as, for example, a slip or thread male or female luer adapter, or another suitable connector. In some embodiments, the distal end 74 of the instrument 22 may be blunt and/or tapered. In some embodiments, the distal connector 34 may be configured to couple to a proximal end of a catheter adapter. In some embodiments, the syringe 12 may be coupled to a proximal end of the catheter adapter 32 of the catheter assembly 30 (illustrated, for example, in FIGS. 1A-1B and 2A-2B), and the plunger 16 may be depressed to advance the instrument 22 in the distal direction such that the instrument 22 is disposed in a fluid pathway of the catheter assembly 30 and/or advanced beyond the distal end 48 of the catheter 36.

In some embodiments, a method of operating the delivery device 102 may include coupling the delivery device 102 to the proximal end of the catheter adapter 32. In some embodiments, the plunger 16 may be depressed to advance the instrument 22 in the distal direction, which may also cause the liquid 38 to flow from the inner barrel 106 through the first valve 108 into the outer barrel 104. In some embodiments, depressing the plunger 16 may also move the inner barrel 106 to the distal position, closing the second valve 110. In some embodiments, the plunger 16 may then be retracted or moved proximally, at least partially retracting the instrument 22 in the proximal direction. In some embodiments, proximal movement of the plunger 16 may also move the inner barrel 106 proximally, opening the second valve 110. In some embodiments, as the plunger is moved proximally, the liquid 38 disposed within the outer barrel 104 may exit the distal opening 46 of the syringe 12 and may flush the catheter assembly 30.

In some embodiments, an inner surface of the outer barrel 104 may include a stop or catch that may prevent the inner barrel 106 from moving proximally beyond the proximal position. In some embodiments, a proximal end of the outer barrel 104 may include a seal 97 proximate an opening in the outer barrel 104 through which the plunger 16 may extend. In some embodiments, the seal 97 may prevent fluid leakage from the proximal end of the outer barrel 194.

In some embodiments, the inner barrel 106 may be fixed within the outer barrel 104 via one or more retaining features. In further detail, in some embodiments, one or more retaining features of the inner barrel 106 may be engaged in a mechanical fit (such as, for example, a snap fit, a press fit, or another suitable fit) with one or more retaining features of the outer barrel 104. In some embodiments, the retaining features may include one or more ribs 99 (illustrated, for example, in FIGS. 8A-8D), which may extend from the inner barrel 106 to the outer barrel 104. In some embodiments, the ribs 99 may be rigid or semi-rigid. In some embodiments, the retaining features may be annular and may extend around a circumference of the inner barrel 106. In these and other embodiments, the retaining features may include apertures and/or valves which may open in response to fluid pressure, allowing fluid to pass. In some embodiments, fluid may flow around the retaining features.

In some embodiments, a proximal end of the inner barrel 106 may include one or more retaining features 111. In some embodiments, the proximal end of the inner barrel 106 may include a single annular retaining feature 111. In some embodiments, the retaining features 111 may contact the plunger 16 to prevent proximal movement of the plunger 16. In some embodiments, the distal opening 46 may include an anti-reflux valve, which may prevent blood reflux from entering the delivery device 102.

Figure 10A:
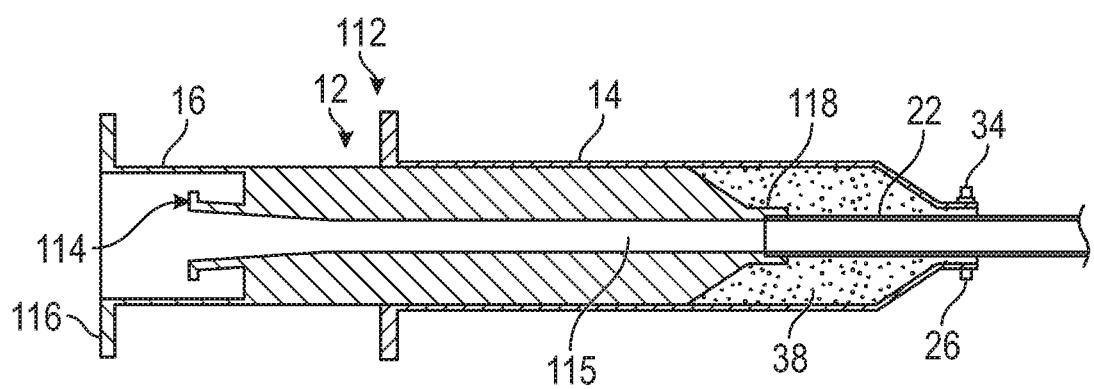
FIG. 10A is a cross-sectional view of another example delivery device, illustrating an example plunger in a proximal position, according to some embodiments.
Figure 10B:
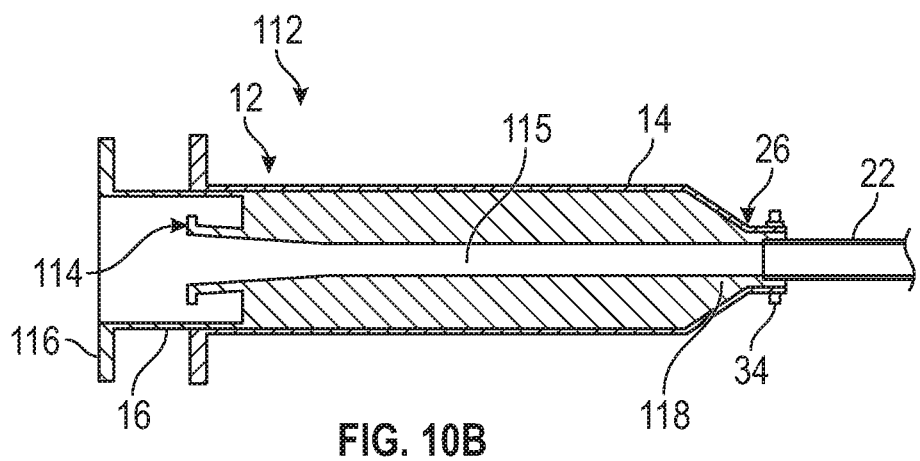
FIG. 10B is a cross-sectional view of the delivery device of FIG. 10A, illustrating the plunger in a distal position, according to some embodiments.

Referring now to FIGS. 10A-10B, another example delivery device 112 is illustrated, according to some embodiments. In some embodiments, the delivery device 112 may include or correspond to one or more of the following: the delivery device 10, discussed with respect to FIGS. 1-3; the delivery device 58, discussed with respect to FIGS. 4-5; the delivery device 72, discussed with respect to FIGS. 6-7; the delivery device 88, discussed with respect to FIG. 8; and the delivery device 102 discussed with respect to FIG. 9. In further detail, in some embodiments, the delivery device 112 may include one or more features of one or more of the following: the delivery device 10, the delivery device 58, the delivery device 72, the delivery device 88, and the delivery device 102. In some embodiments, one or more of the following may include one or more features of the delivery device 112: the delivery device 10, the delivery device 58, the delivery device 72, the delivery device 88, and the delivery device 102.

In some embodiments, the plunger 16 may include a connector 114. In some embodiments, the connector 114 may include a luer adapter, such as a slip or thread male or female luer adapter, or another suitable connector. In some embodiments, a channel 115 may extend from the connector 114 through a distal end of the plunger 16. In some embodiments, the connector 114 may be disposed within the plunger 16. In some embodiments, the connector 114 may be disposed distal to a proximal end 116 of the plunger 16.

In some embodiments, the instrument 22 may extend from a distal end 118 of the plunger 16. In some embodiments, the channel 115 may provide a fluid pathway for fluid infusion and/or blood withdrawal. In some embodiments, a blood collection device or a fluid infusion device may be coupled to the connector 114. In some embodiments, a distal end of an extension tube may be coupled to the connector 114. In some embodiments, a proximal end of the extension tube 120 may be coupled to the blood collection device or the infusion device. In some embodiments, the extension tube 120 may be in fluid communication with the channel 115 to provide a fluid pathway for fluid infusion and/or blood withdrawal.

In some embodiments, the distal end 26 of the syringe 12 may include a distal connector 34, such as, for example, a slip or thread male or female luer adapter, or another suitable connector. In some embodiments, the distal connector 34 may be configured to couple to a proximal end of a catheter adapter. In some embodiments, the syringe 12 may be coupled to a proximal end of the catheter adapter 32 of the catheter assembly 30 (illustrated, for example, in FIGS. 1A-1B and 2A-2B), and the plunger 16 may be depressed to advance the instrument 22 in the distal direction such that the instrument 22 is disposed in a fluid pathway of the catheter assembly 30 and/or advanced beyond the distal end 48 of the catheter 36.

Figure 10C:
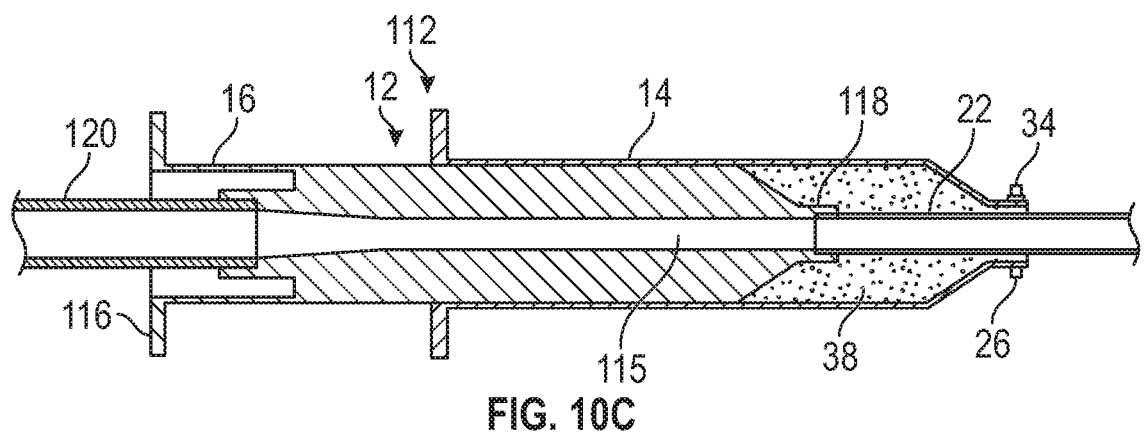
FIG. 10C is a cross-sectional view of the delivery device of FIG. 10A, illustrating an example extension tube integrated within the plunger, according to some embodiments.

Referring now to FIG. 10C, in some embodiments, a distal end of an extension tube 120 may be integrated into the plunger 16. In some embodiments, a proximal end of the extension tube 120 may be coupled to a blood collection device or an infusion device. In some embodiments, the extension tube 120 may be in fluid communication with the channel 115 to provide a fluid pathway for fluid infusion and/or blood withdrawal.

Figure 11:
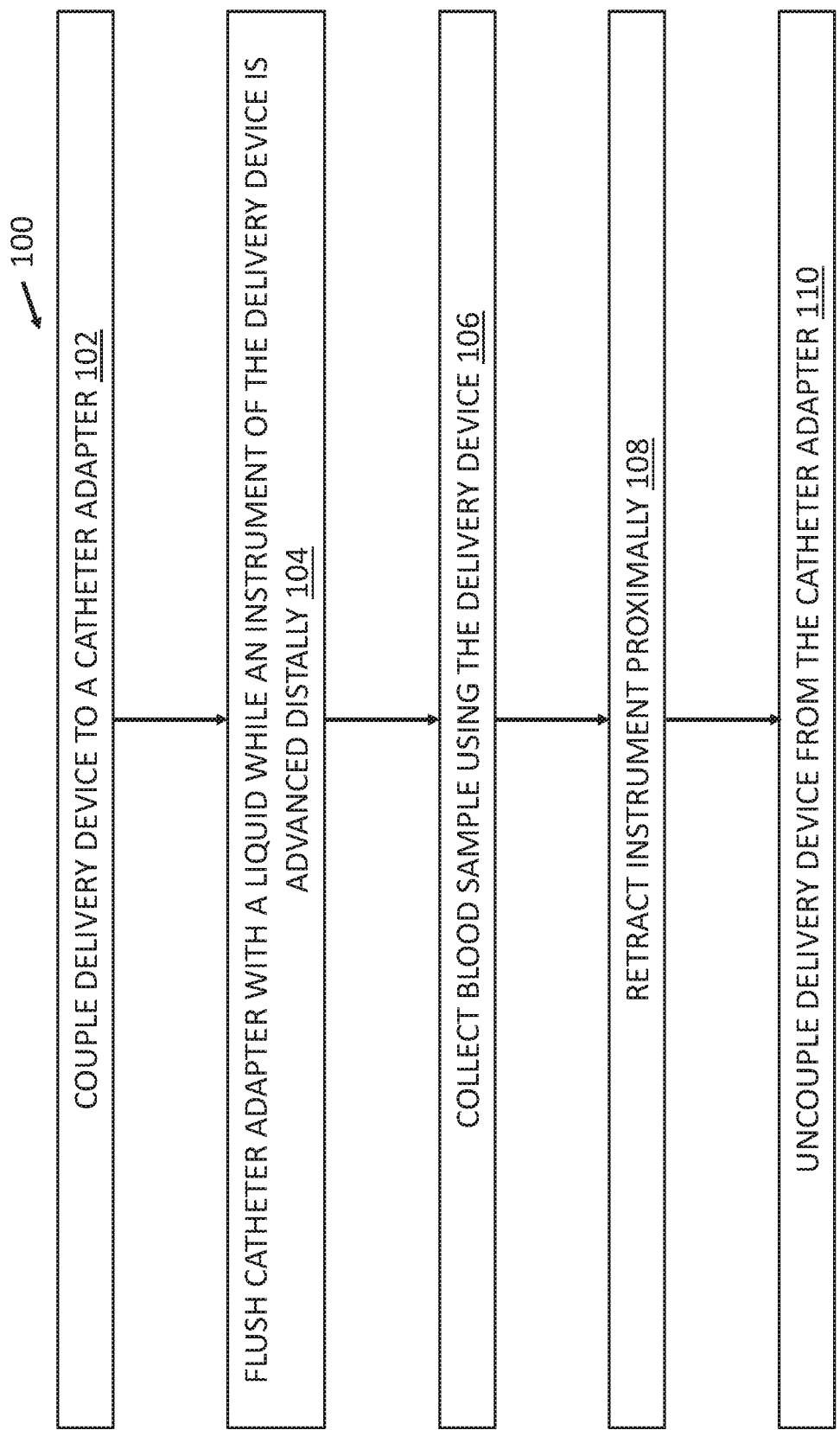
FIG. 11 is a flow chart illustrating an example method, according to some embodiments.

Referring now to FIG. 11, an example method 100 is illustrated, according to some embodiments. In some embodiments, the method 100 may begin at block 102. In block 102, a delivery device may be coupled to a catheter adapter. The delivery device may include or correspond to the delivery device of one or more of FIGS. 1-10. In some embodiments, the delivery device may be coupled to the catheter adapter via a needleless connector and/or an interface connector, such as the interface adapter 60 of FIGS. 4A-4B, for example.

In some embodiments, block 102 may be followed by block 104. At block 104, the catheter adapter may be flushed with a liquid, such as, for example, saline or another suitable flushing liquid, while an instrument of the delivery device is advanced distally. In some embodiments, the instrument of the delivery device may be advanced distally into the vasculature of the patient. The instrument may include or correspond to the instrument 22 of one or more of FIGS. 1-10. In some embodiments, the catheter adapter may be flushed with the liquid and the instrument may be advanced distally by depressing a plunger of the delivery device.

In some embodiments, block 104 may be followed by block 106. In block 106, a blood sample may be collected using the delivery device. In some embodiments, the blood sample may be collected in a blood collection device coupled to the delivery device.

In some embodiments, block 106 may be followed by block 108. In block 108, the instrument may be retracted proximally. In some embodiments, a distal end of the instrument may be disposed within the delivery device or the interface adapter when the instrument is retracted proximally.

In some embodiments, block 108 may be followed by block 110. In block 110, the delivery device may be uncoupled from the catheter adapter. Although illustrated as discrete blocks, various blocks of method 100 may be divided into additional blocks, combined into fewer blocks, or eliminated, depending on the desired implementation. For example, block 108 may be eliminated in some embodiments.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A delivery device for delivering an instrument into a catheter assembly, comprising:
    a syringe having a barrel and a plunger movable within the barrel;
    a guide feature disposed within the barrel and movable with the plunger, wherein the guide feature comprises a channel, wherein the channel is generally U-shaped; and an instrument disposed within the barrel and extending through the channel, wherein in response to depression of the plunger, the guide feature moves in a distal direction, the instrument moves through the channel, and a first end of the instrument is advanced in the distal direction, wherein a second end of the instrument is fixed.

2. The delivery device of claim 1, wherein the instrument comprises a catheter or a probe.

3. The delivery device of claim 1, wherein the barrel comprises a liquid, wherein in response to the depression of the plunger, the liquid exits a distal opening of the syringe, wherein a diameter of the distal opening of the syringe is greater than an outer diameter of the instrument.

4. The delivery device of claim 1, wherein the second end of the instrument is fixed within the barrel.

5. The delivery device of claim 1, further comprising an interface adapter coupled to the syringe, wherein the second end of the instrument is fixed within the interface adapter.

6. The delivery device of claim 1, wherein in response to the depression of the plunger, the guide feature is moved in the distal direction a first distance, and the first end of the instrument is advanced in the distal direction a second distance, wherein the second distance is greater than the first distance.

7. The delivery device of claim 1, wherein the first end of the instrument is advanced in the distal direction beyond a distal end of the syringe in response to the plunger being partially or fully depressed.

8. The delivery device of claim 1, wherein the syringe further comprises extension tubing extending outwardly from a distal portion of the syringe, wherein the second end of the instrument is coupled to the extension tubing, wherein the instrument comprises a catheter.

9. The delivery device of claim 1, wherein the instrument comprises a catheter, further comprising a guidewire disposed within the catheter, wherein in response to the depression of the plunger, the guidewire and the catheter move through the channel and a first end of the guidewire is advanced in the distal direction, wherein a second end of the guidewire is fixed.

10. The delivery device of claim 9, wherein the first end of the guidewire is advanced in the distal direction beyond a distal end of the syringe in response to the plunger being partially or fully depressed.

11. The delivery device of claim 9, wherein in response to the depression of the plunger, the guide feature is moved in the distal direction a first distance, and the first end of the guidewire is advanced in the distal direction a second distance, wherein the second distance is greater than the first distance.

12. The delivery device of claim 1, further comprising support tubing extending from the guide feature and coupled to the guide feature, wherein in response to the depression of the plunger, the guide feature is moved in the distal direction a first distance, the instrument moves through the support tubing, and a first end of the support tubing is advanced in the distal direction the first distance.

\* \* \* \* \*